United States Patent [19]

Sachs et al.

[11] Patent Number: 5,942,409
[45] Date of Patent: Aug. 24, 1999

[54] PROCESS FOR IDENTIFICATION OF SUBSTANCES MODULATING UREI DEPENDENT MECHANISMS OF HELICOBACTER PYLORI METABOLISM

[75] Inventors: George Sachs, Encino, Calif.; Klaus Melchers, Aach, Germany

[73] Assignee: Byk Gulden Lomberg Chemische Fabrik GmbH, Konstanz, Germany

[21] Appl. No.: 09/126,326

[22] Filed: Jul. 31, 1998

[51] Int. Cl.[6] .............. C12Q 1/18; C12Q 1/58; C12Q 1/02; C12Q 1/00

[52] U.S. Cl. .............. 435/32; 435/12; 435/29; 435/4

[58] Field of Search .............. 435/32, 12, 29, 435/4

[56] References Cited

U.S. PATENT DOCUMENTS

| 4,882,271 | 11/1989 | Evans et al. | 435/12 |
|---|---|---|---|
| 5,556,760 | 9/1996 | Nakamura et al. | 435/12 |
| 5,702,911 | 12/1997 | Whalen | 435/12 |
| 5,804,549 | 9/1998 | Blackburn et al. | 514/2 |

OTHER PUBLICATIONS

Skouloubris et al., *Infection and Immunity*, "The Helicobacter pylori UreI Protein Is Not Involved in Urease Activity by Is Essential for Bacterial Survival In Vivo", Sep. 1998, pp. 4517–4521.

*Primary Examiner*—Louise N. Leary
*Attorney, Agent, or Firm*—Jacobson, Price, Holman & Stern, PLLC

[57] ABSTRACT

The present invention provides a screening process for the identification of anti-helicobactericidal substances modulating ureI dependent mechanisms of gastric Helicobacter metabolism. Gastric Helicobacter cells are treated with a substance to be tested for modulating ureI dependent mechanisms of gastric Helicobacter metabolism and gastric Helicobacter acid resistance or sensitivity to urea is determined.

18 Claims, 7 Drawing Sheets

FIG. 1
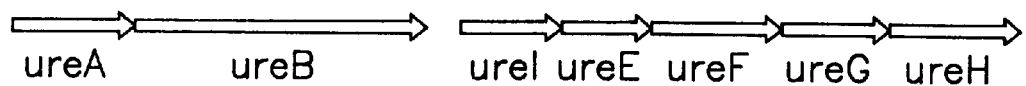
ure operon (wild-type)
ure kan$^R$ $\Delta$ureI operon
FIG. 2
[kD]
98 —
64 —

PROCESS FOR IDENTIFICATION OF SUBSTANCES MODULATING UREI DEPENDENT MECHANISMS OF HELICOBACTER PYLORI METABOLISM

TECHNICAL FIELD

The invention relates to a process for identification of substances modulating ureI dependent mechanisms of gastric Helicobacter metabolism and provides different kinds of assays for carrying out such process. In particular the process according to the invention allows the identification of substances inhibiting ureI dependent mechanisms of gastric Helicobacter metabolism. Substances identified in a process according to the invention as modulating ureI dependent mechanisms are suitable for the production of medicaments for the treatment of gastric Helicobacter related diseases.

PRIOR ART

Helicobacter pylori (herein also referred to as H. pylori), a gastric Helicobacter, is a gram-negative, spiral-shaped, highly motile bacterium thriving in the human stomach [Warren & Marshall (1983) Lancet, I:1273–1275; Schade et al. (1994) Gastroenterol 107, 180–188]. The latter provides an environment of varying acidity due to secretion of protons by action of the gastric H,K ATPase. Thus gastric Helicobacters such as H. pylori must have developed specialized acid-protective mechanisms.

This microorganism is now known as the causative agent of gastric diseases as gastritis and peptic ulcers. In addition, an association of H. pylori infection with gastric cancer is also apparent [Cover & Blazer (1995) ASM News 61, 21–26]. Eradication of H. pylori from peptic ulcer patients by antibiotic therapy reduced recurrence of ulcers to less than 10%. Today eradication triple therapy needs inhibition of acid secretion and the action of two antibiotics while antibiotic therapy without use of drugs inhibiting acid secretion fail to eradicate H. pylori from the human stomach. The synergistic effect of proton pump inhibition and antibiotic therapy presumably results from stimulation of H. pylori growth by elevation of pH in the stomach making the pathogen more susceptible to standard antibiotics. The latter is due to the fact that action of these drugs is more efficient in growing bacterial populations characterized by high level synthesis of cellular compounds (Sachs et al (1997) Digestion 58, suppl. 1, 8–13).

There are several problems arising from triple therapy. First of all compliance is a problem because three different drugs have to be taken from the patient for a week. Second, every drug has a distinctive pattern of side effects and in H. pylori eradication therapy the side effects of the three compounds add to each other and there is also a potential for adverse effects by synergism of side effects and/or drug interaction. Third, due to the use of broad spectrum antibiotics with the negative action of the drugs on the resident bacterial microflora H. pylori triple therapy contributes to the emerging problem of resistance and cross-resistance. In conclusion from the above there is a medical need for new substances appropriate for H. pylori eradication and these new drugs should avoid the problems of standard antibiotic therapy, especially the development of resistance and the problems associated with multiple drug therapy. An ideal anti-helicobactericidal drug should, therefore, have selective character which means that this drug would inhibit H. pylori but not the bacterial population of the microflora of the lower intestine. A prerequisite enabling screening for such an ideal drug would be that the molecular target is unique for H. pylori. Thus a better understanding of H. pylori molecular biology and physiology will help to detect putative potential H. pylori-specific targets.

Potential H. pylori drug targets should relate to the unique characteristics of the bacterium which are employed for survival of the pathogenic bacterium in its natural ecological niche, the acidic environment of the human stomach. A feature of H. pylori is high level expression of urease, a nickel-metallo enzyme [Mobley et al. (1995) Microbiol Rev 59, 451–480]. Urease has been shown to confer acid resistance to the bacterium in-vitro [Clyne et al. (1995) Infect Immun 63, 1669–1673]. In animal models it has been demonstrated that the enzyme is essential for colonization and perhaps even persistence of an infection in the gastric mucosa making this enzyme activity to a potential target for anti-bacterial research [Tsuda et al. (1994) Infect Immun 62, 3586–3589; Eaton & Krakowka (1994) Infect Immun 62, 3604–3607]. In recent studies it has been shown that urease mediates acid resistance to the bacterium by maintaining a proton motive across (p.m.f.) the inner cytoplasmic membrane [Meyer-Rosberg et al. (1996) Gastroenterol 111, 886–900; Scott et al. (1998) Gastroenterol 114, 58–70].

Ureases are also present in other bacterial species as for example Proteus vulgaris, Proteus mirabilis, Klebsiella aerogenes, Yersinia enterocolitica, Ureaplasma urealyticum, and Bacillus subtilis sp.TB-90. Since the other known urease-producing bacterial species are nongastric one can speculate that differences of the urease primary sequences, in the gene composition of the urease gene clusters and/or in the regulation of urease expression and/or of the enzyme activity might relate to the different environments of these bacteria. For example it has been demonstrated that expression of the Klebsiella urease operon is under control of ntr (nitrogen regulation system) whereas plasmid-encoded urease genes are urea-inducible. In contrast it is well known that the A2B2 multimeric urease of H. pylori is expressed constitutively at high levels.

As found for the other ureases, the H. pylori enzyme yields ammonia and carbonic acid by hydrolysis of urea. The enzyme of the gastric bacterium is encoded by the ure operon, a gene cluster containing seven open reading frames, ureABIEFGH. ureA and ureB encode the two structural protein subunits UreA and UreB. The other five genes, ureIEFGH, encode accessory proteins. Nucleotide sequences of ureIEFGH are disclosed in WO 93/07273. For most of the latter proteins a function in urease assembly and nickel-insertion into the urease-apoenzyme is postulated while a function of the ureI gene product has not been described. However, recent publication pointed to the fact that the H. pylori ureI predicted protein exhibits some homology to bacterial AmiS transport proteins, the latter postulated to mediate transmembrane influx of amidase substrates (Wilson et al. (1995) J Biol Chem 270 (32), 18818–18824). Strikingly, sequences homologous to ureI were not present in all urease loci cloned from other bacteria. Another feature of the ureI-encoded amino acid sequences is that the predicted protein has several putative transmembrane segments indicating that the protein might act as a membrane associated transport protein.

Bacterial urease enzymes are thought to be localized in the cytoplasm contributing to nitrogen metabolism. In contrast, the urease enzyme of H. pylori, although present in the cytoplasm, was partly found associated with the outer membrane of the bacterium. It was claimed in earlier studies that the H. pylori enzyme is therefore an apparent exception to the rule that ureases are cytoplasmic enzymes and that the external localization is consistent with the fact that the enzyme has to elevate outside pH when *H. pylori* is exposed to acid [Phadnis et al. (1995) Infect Immun 64, 905–912]. However, recently published studies show that the enzyme is not active in pH less than 4 bringing into question a role of cell surface urease for acid survival. In these studies it was found that urease activity associated with intact *H. pylori* cells is activated when the medium pH drops below 6.0 [Scott et al. (1998) Gastroenterol 114, 58–70]. Thus it seems to be internal urease of *H. pylori* which is activated by external acidic pH but the mechanism of activation of enzyme activity is not known. It was also demonstrated that ureases activity maintains metabolism and membrane potential under acidic external pH [Scott et al. (1998) Gastroenterol 114, 58–70; Scott et al., in *H. pylori:* Basic mechanisms to clinical cure 1998 (eds. Hunt et al.) Kluwer Academic Press, London 1998; p. 133–147]. In a preliminary study, Reuse and coworkers (Reuse et al.; Abstract, 3rd International Workshop on pathogenesis and host response in Helicobacter infections, Helsingor, Denmark 1998) claimed that the ureI gene product is a membrane transport protein which is essential for colonization of a gastric environment but the exact molecular function of the protein and the nature of it's physiological role in *H. pylori* biology remains unsolved.

SUMMARY OF THE INVENTION

A screening process is provided for identification of anti-helicobactericidal substances modulating ureI dependent mechanisms of gastric Helicobacter metabolism. Gastric Helicobacter cells are treated with a substance to be tested for modulating ureI dependent mechanisms of gastric Helicobacter metabolism, and gastric Helicobacter acid resistance or sensitivity to ureI is determined.

BRIEF DESCRIPTION OF THE DRAWINGS

FIG. 1 depicts the organization of the urease operon in *H. pylori* wild-type cells and in ureI-deficient mutants.

FIG. 2 shows expression of ureB gene product (ureB protein) in *H. pylori* cells.

DESCRIPTION OF THE INVENTION

Figure 3:
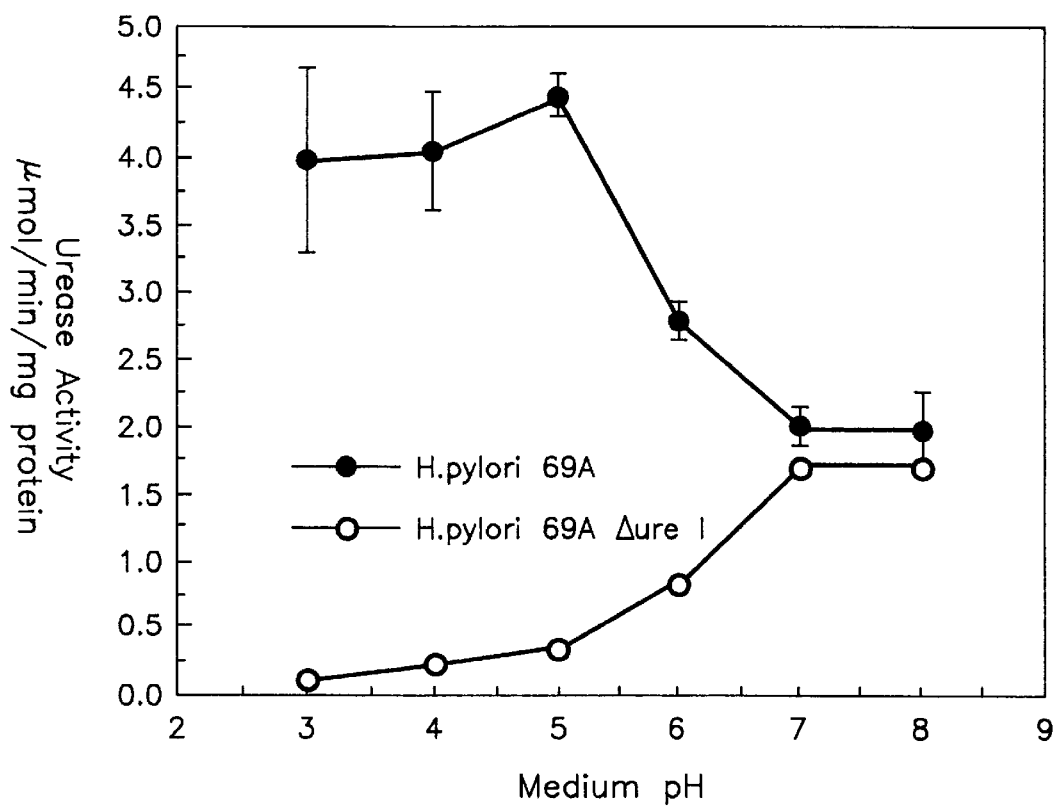
FIG. 3 graphically compares the pH optimum of bacterial urease activity in intact organisms of *H. pylori* 69A and *H. pylori* 69A ureI knock-out mutant.

Surprisingly it has been found now that the ureI gene encodes a protein which is essentially involved in the mechanism of acid-stimulation of *H. pylori* urease activity as well as maintenance of metabolism and acid resistance, especially when *H. pylori* cells were exposed to media of high acidity (below pH 4.0). Thus this enzyme controls key elements which are thought to be essential for *H. pylori* acid survival. A *H. pylori* ureI knock-out mutant was constructed where the open reading frame (hereinafter referred to as ORF) of ureI was substituted for the ORF of a kanamycin resistance cassette resulting in a ureAB-kanR-EFGH gene loci in the mutants. The mutated *H. pylori* strains, under neutral medium conditions, were identical to the corresponding wild-type strains. They were shown to express an active urease enzyme to levels which were present in the wild-type. pH-adapted cells with the urease operon lacking the ureI gene also showed increase of urease enzyme activity in the range of moderate medium acidity. When the medium was adjusted to higher acidity urease activity collapsed and metabolism of cells was inhibited. This resulted in the loss of bacterial viability. The latter effects, namely inhibition of urease activity and metabolism in the ureI-negative strains with therefore cell death, are in contrast to the corresponding wild-type cells which survive these acid challenge experiments. These experiments were performed with non-dividing *Helicobacter pylori* populations showing that the absence of ureI (which mimicks full inhibition of the ureI gene product) is lethal even for non-dividing cells in an acidic environment depending on the distinct experimental conditions (especially in the presence or absence of strong buffer).

Given the relevance of ureI for urease pH regulation and therefore controlled acid resistance and maintenance of metabolism in an environment of acidity, the findings obtained and described here allow the screening for anti-helicobactericidal substances. Preferentially these anti-helicobactericidal substances are directed against ureI-dependent mechanisms maintaining bacterial metabolism and viability in acidic media especially ureI-dependent mechanisms of *H. pylori* urease activation. Given the results described herein there are distinct ways to design assays suitable to find substances interacting with the ureI gene or gene product or mechanisms the UreI protein is involved in. Basis of such assays is the resistance of *H. pylori* to acid. Treatment of *H. pylori* with a substance with activity directed towards ureI expression and/or UreI function of *H. pylori* would result in increased sensitivity of *H. pylori* to acid. *H. pylori* with substance-mediated decrease or inhibition of ureI gene expression and/or UreI protein function would show decreased capacity to resist against acid when compared to untreated wild-type cells. A screen for inhibitors can thus make use of distinct responses of a *H. pylori* cell population treated with a substance with activity directed towards ureI expression and/or UreI function of *H. pylori*. As will be obvious to one skilled in the art for detection and characterization of such substances a combination of the procedures and assays described herein can be used. *H. pylori* ureI knock-out mutants (or similar ureI mutants) can be used as a control mimicking the effect of compounds leading to full absence of ureI function.

In one aspect the invention is therefore related to a screening process for the identification of anti-helicobactericidal substances comprising treating under acidic conditions gastric Helicobacter cells carrying a functional urease operon with at least one substance to be tested for anti-helicobactericidal activity and determining the gastric Helicobacter acid resistance.

Anti-helicobactericidal substances in connection with the present invention relates to substances with inhibiting activity on gastric Helicobacter. It is preferred that the anti-helicobactericidal activity of the substance to be tested is directed against ureI dependent mechanisms of gastric Helicobacter metabolism. It is preferred that such ureI dependent mechanisms of gastric Helicobacter metabolism are either inhibited or activated by the anti-helicobactericidal substances.

In another aspect the invention is therefore related to a screening process for the identification of substances inhibiting ureI dependent mechanisms of gastric Helicobacter metabolism comprising treating under acidic conditions gastric Helicobacter cells carrying a functional urease operon with at least one substance to be tested for inhibiting ureI dependent mechanisms of gastric Helicobacter metabolism and determining the gastric Helicobacter acid resistance.

In connection with the present invention gastric Helicobacter refers to strains classified as Helicobacters, gram-negative bacteria thriving in a gastric environment. Examples to be mentioned are *Helicobacter pylori, Helicobacter heilmanii* and *Helicobacter felis* whereby *Helicobacter pylori* is preferred.

In connection with the present invention ureI dependent mechanisms of gastric Helicobacter metabolism refers to mechanisms of metabolisms of gastric Helicobacter which are related to the expression of ureI and/or function (activity) of the ureI gene product. It is preferred that such ureI dependent mechanisms of gastric Helicobacter metabolism are essential for viability of the gastric Helicobacter, preferentially in acidic media. It is further preferred that ureI dependent mechanisms of gastric Helicobacter relates to an ureI dependent urease activation in the gastric Helicobacter in acidic media.

In connection with the present invention acidic conditions refers to conditions where a pH below 7 is present. Preferentially acidic conditions refers to a liquid or solid media with a pH below 7. Especially preferred are aqueous medium. As will be obvious from below the ideal pH present in the process according to the invention will depend on the gastric Helicobacter strain used and the procedure of determining acid resistance of the gastric Helicobacter. Such ideal pH can be determined by one skilled in the art according to a method described below.

It is further preferred that in the process according to the invention urea is present, in aqueous media preferentially in a concentration range between 1 and 20 mMol. Additionally further components usually present in *H. pylori* growth media can be present.

In one embodiment of the invention these aqueous media contain strong buffers adjusted to a pH below 7, preferentially to a pH between 1.5 and 6.5 especially preferred between 3 and 5. Exemplary buffers which are suitable in connection with the invention are for example citric acid/ phosphate buffers, phosphate buffers, HEPES buffers (N-2 (2-hydroxyethyl)piperazine-N'(2-ethanesulfonic acid) and MES buffers (2-(N-Morpholino)ethane sulfonic acid) preferentially in a concentration range of 50–250 mM depending on pH and buffer used.

In connection with the present invention gastric Helicobacter cells carrying a functional urease operon refers to gastric Helicobacter cells which are capable of expressing an active urease and having elevated levels of urease enzyme activity under acidic conditions, especially under acidic conditions in the pH range of 1 to 4 (absence of buffer or in weak buffer) or below 6.5 (in strong buffer) (depending on the strain and experimental design used). Examples to be mentioned are *H. pylori* wild-type strains with urease activity, such as *H. pylori* 69A, *H. pylori* ATCC 49504 or *H. pylori* ATCC 49503.

Gastric Helicobacter acid resistance in connection with the present invention refers to bacterial mechanisms maintaining metabolism and viability in acidic media containing urea.

Gastric Helicobacter acid resistance in connection with the invention can be determined by procedures which assay parameters indicative for bacterial metabolism and viability during or after acid exposure. Examples to be mentioned in connection with the present invention are growth experiments, the determination of metabolic or bioenergetic parameters such as enzyme activity, activity of general energy and/or substrate mechanism and production of biomolecules such as protein, DNA and/or RNA. In connection with the invention it is particularly preferred to determine urease-mediated pH changes in cellular compartments of gastric Helicobacter or in the environment of gastric Helicobacter (media surrounding gastric Helicobacter) or use growth experiments.

Urease-mediated pH changes in cellular compartments of gastric Helicobacter or in the environment of gastric Helicobacter can be determined for example by using pH sensitive dyes. The use of dyes for detection and measurement of effects on the pH by *H. pylori* metabolism and urease activity is described in detail by Meyer-Rosberg et al. (1996) and Scott et al. (1998). In strong buffers supplemented with urea, incubation of *H. pylori* cells with urease activity does not led to significant changes of medium pH but one can use pH sensitive fluorescent dyes for detection of urease-mediated pH changes in cellular compartments of *H. pylori* (Meyer-Rosberg et al., 1996). One can use pH indicative dyes which are membrane permeant or membrane impermeant. An example of the latter is the use of BCECF (bis-carboxyethyl carboxy fluorescein). BCECF is a dual wavelength excitation dye, 450 nm is isobestic, 480 nm the pH dependent excitation and 530 nm emission. It is relatively membrane impermeant and is therefore able for measurement of pH outside the cytoplasmic membrane of *H. pylori*. It is therefore particularly preferred to use BCECF fluorescence for determining urease-mediated pH changes especially when strong buffers are used in the process according to the invention. It is preferred to measure these urease-mediated pH changes in media containing strong buffers at neutrality (pH 7) and at moderate acidity (pH 5) to distinguish between ureI-independent and ureI-dependent pH changes.

As shown herein in the absence of strong buffer the ureI-dependent activation of *H. pylori* 69A urease leads to a significant elevation of medium pH when the medium pH is pre-adjusted to pH 2.0 but pH elevation was independent on ureI when *H. pylori* 69A was added to media supplemented with urea and adjusted to pH 4.0. The pH where the ureI-dependent and ureI-independent acid-activation of urease enzyme separates depends, to some extent, on the strain used and can for example be determined experimentally using the method described herein. An assay based on the elevation of medium pH can be transferred to microwell titer plate suitable for high throughput screening. H. pylori is added to media, adjusted to high acidity where urease activation is ureI-dependent (pH 2.0 is favorable when H. pylori 69A is used) and contained substances to be assayed. UreI-dependent pH shift can be measured by use of pH-sensitive indicator molecules. The presence of substance-mediated ureI inhibition is indicated when a strain is not able elevate medium pH (initially adjusted to pH 2.0) significantly, as compared to the wild-type strain. The substances which interfere with pH elevation in the former type of assay are to be further assayed for their action on H. pylori-induced medium pH elevation in the range of moderate acidity and/or around medium neutrality (in the pH range where bacterial urease enzyme activity is ureI-independent; namely between pH 4.0 through 8.5). This procedure distinguishes substances which attack the urease enzyme and allows selection of substances potentially acting on ureI-dependent and urease-mediated medium alkalinization.

Another read-out of bacterial acid resistance is the ability of a bacterial population to grow after acid exposure. As shown herein, the capacity of H. pylori ureI knock-out mutants to grow after incubation in media supplemented with urea is significantly reduced or even absent depending on medium acidity and incubation time. On the basis of the growth experiments described below in detail for H. pylori 69A and ureI-deficient derivatives, H. pylori acid incubation can be performed in the presence of at least one substance to be tested for modulating ureI dependent mechanisms of Helicobacter pylori metabolism with afterwards transfer of small aliquots of treated cells into substance-free growth medium and incubation under standard growth conditions for detection of survival and substance-mediated inhibition of survival (that means no or reduced bacterial growth can be detected compared to the growth of H. pylori cells not pretreated with the substance). Bacterial growth can be detected using several parameters indicative for viable bacterial cells, as for example optical density.

Cytosensor experiments which employ a perfusion microphysiometer system are able to detect small changes of medium pH as a function of bacterial metabolic activity. The primary read-out is in mV and mV changes correlate to changes of medium pH due to bacterial metabolism. Thus the system allows detection of changes in the metabolic activity of living bacteria and changes thereof. Perfusion microphysiometry detects responses of H. pylori to environmental changes such as medium pH, medium urea or addition of compounds to the medium. Since the repertoire of physiological capacity of H. pylori (and all other bacteria) depends on the given genetic constitution of the microorganism(s) microphysiometry is able to detect absence or presence of specific vital mechanisms of the bacterium, as shown herein for function of the ureI gene.

As disclosed above Helicobacter pylori strains lacking the ureI gene were shown to have urease activity at neutral conditions or slightly acidic conditions. A substance selectively inhibiting ureI dependent urease activation in Helicobacter pylori in acidic media is expected to inhibit urease activity under neutral or slightly acidic conditions which means conditions where urease activation is independent of ureI. Thus treating under such conditions Helicobacter pylori cells carrying a functional urease operon with a substance identified to decrease acid resistance of Helicobacter pylori under acidic conditions will allow to identify substances which inhibit urease activity independently from ureI expression and/or activity of the ureI gene product. Substances which inhibit urease activity under essentially neutral conditions are thus not selective inhibitors of ureI dependent activation of urease in Helicobacter pylori.

In a further aspect the invention is therefore related to a screening process for the identification of anti-helicobactericidal substances comprising treating under acidic conditions gastric Helicobacter cells carrying a functional urease operon with at least one substance to be tested for anti-helicobactericidal activity, determining the gastric Helicobacter acid resistance and treating under conditions where gastric Helicobacter urease-activation is ureI-independent gastric Helicobacter cells carrying a functional urease operon with said substance to be tested for anti-helicobactericidal activity and determining the gastric Helicobacter urease activity.

Preferentially such screening process is related to the identification of substances inhibiting ureI dependent mechanisms of gastric Helicobacter metabolism comprising treating under acidic conditions gastric Helicobacter cells carrying a functional urease operon with at least one substance to be tested for inhibiting ureI dependent mechanisms of gastric Helicobacter pylori metabolism, determining the gastric Helicobacter acid resistance and treating under conditions where gastric Helicobacter urease-activation is ureI-independent gastric Helicobacter cells carrying a functional urease operon with said substance to be tested for modulating ureI dependent mechanisms of gastric Helicobacter metabolism and determining the gastric Helicobacter urease activity.

Conditions where gastric Helicobacter urease-activation is ureI-independent in connection with the present invention preferentially refers to conditions with a pH between 4.0 and 8.5. Especially preferred is pH 7. The pH where the ureI-dependent and ureI-independent acid-activation of urease enzyme separates depends, to some extent, on the strain and procedure used and can for example be determined experimentally using a method described herein.

Urease activity can be determined according to procedures known to one skilled in the art for example by using labeled urea, use of pH indicators or determining ammonia concentration.

The substance to be tested in connection with the process according to the invention is employed in an usual concentration range, especially preferred in a range of 1 to 50 $\mu$mol/L.

Further activation of ureI of gastric Helicobacter in the presence of conditions where gastric Helicobacter urease-activation is ureI-independent and in the presence of urea will be lethal to gastric Helicobacter. Based on these findings a screening process can be designed to identify anti-helicobactericidal substances especially such substances activating ureI dependent mechanisms of gastric Helicobacter.

In another aspect the invention is related to a screening process for the identification of anti-helicobactericidal substances comprising treating under conditions where gastric Helicobacter urease-activation is ureI-independent gastric Helicobacter cells carrying a functional urease operon with at least one substance to be tested for anti-helicobactericidal activity and determining the growth sensitivity of the gastric Helicobacter to urea.

Preferentially such screening process is related to the identification of substances activating ureI dependent mechanisms of gastric Helicobacter metabolism comprising treating under conditions where gastric Helicobacter urease-activation is ureI-independent gastric Helicobacter cells carrying a functional urease operon with at least one substance to be tested for activating ureI dependent mechanisms of gastric Helicobacter metabolism and determining the growth sensitivity of the gastric Helicobacter to urea.

As a control system the *H. pylori* mutants with non-polar ureI knock-out mutation is to be used. These cells have urease enzyme activity at neutral pH (which is independent of ureI) to levels as observed for the corresponding wild-type strains. Thus substance-induced activation of ureI activity with therefore increase of urease activity under conditions which are normally independent of ureI would increase urease activity only in strains capable of expressing the activity ureI gene product. A compound which is able to elevate urease activity of wild-type *H. pylori* in a pH range where ureI is not active but fails to activate urease enzyme activity of corresponding *H. pylori* mutants lacking ureI is a potential activator of ureI function. Increased urease enzyme activity at neutral pH can be measured via urease activity or increase of *H. pylori* sensitivity of growth or metabolism to urea.

Substances identified to increase neutral pH urea sensitivity or neutral pH urease enzyme activity (between pH 6.5 through 8.5, whereby a pH between 7.0 and 8.0 is preferred) of gastric Helicobacter to urea under such conditions are thus substances activating ureI dependent mechanism of Helicobacter.

Growth sensitivity of the gastric Helicobacter to urea can be determined according to procedures known to one skilled in the art. For example the minimal inhibitory concentration of medium urea (MIC urea) for growth of a given *H. pylori* wild-type cell and the corresponding nonpolar ureI knock-out mutant can be determined according to standard procedures. Subsequently bacteria are grown in the presence of significant but non-inhibitory concentrations of urea in presence of substances to be tested. Controls are grown in the absence of urea but presence of substances. Substances which do not effect growth of *H. pylori* in the absence of urea as well as growth of the mutant in the presence of urea but inhibit growth of the wild-type bacteria in the presence of urea are activators of ureI function.

The process according to the invention can be run in distinct scales (experimental laboratory assay as well as high throughput assays employing robotic technology) depending on the requirements of individual laboratories. High throughput assays are especially preferred in connection with the determination of urease-mediated pH changes in cellular compartments of gastric Helicobacter or in the environment of gastric Helicobacter (media surrounding gastric Helicobacter) or in connection with growth experiments.

Media and standard procedures to be used are as described herein but can be modified according to the varying characteristics of distinct *H. pylori* isolates and laboratory equipment. The growth media, incubation solutions and buffers described herein are especially suitable for the *H. pylori* strains *H. pylori* 69A, *H. pylori* ATCC 43504 and *H. pylori* ATCC 49503.

The process described herein will led to anti-helicobactericidal substances, especially such subsstances interacting with ureI-mediated mechanism of acid-dependent urease activation and ureI-mediated acid survival.

To further analyze the influence of this substances on the ureI gene product the activity of the compounds on UreI can be assayed.

For this purpose the methods described for over-expression of the gene in *H. pylori* and heterologous cells such as *E.coli* are of importance. High-level ureI-expression will be a basis for ureI gene product/drug interaction studies (for example binding of labeled drug to protein). In addition heterologous expression of active *H. pylori* membrane proteins will interfere with the metabolism of the host cell. These methods will allow the further characterization of identified compounds with respect to their activity on UreI without having the molecular nature of ureI activity explained in detail. This protein has homology to membrane proteins involved in transport of amides (Wilson et al. (1995) J Biol Chem 270 (32), 18818–18824X Reuse et al.; Abstract, 3rd International Workshop on pathogenesis and host response in Helicobacter infections, Helsingor, Denmark 1998) and therefor it has been suggested that the *H. pylori* protein acts as a membrane protein mediating trans-membrane flux of substrates such as urea, the substrate of urease. Given that the ureI gene encodes a membrane transport protein elucidation of substrates will provide a parameter for analysis of ureI activity and might be suitable as a readout in the assays described above. However, the ureI gene product is essential at acidic pH for metabolism, urease activity and survival of *H. pylori* under acidic conditions in vitro, as shown by the results of this study.

EXPERIMENTAL

Bacterial strains used

Clinical isolate *H. pylori* strain 69A was a gift of Dr. Rainer Haas, München. Two other *H. pylori* strains used in this study were supplied from the American Type Culture Collection (ATCC, USA). Strains from ATCC were ATCC49503 and ATCC43504. *E.coli* DH5 alpha was from GATC (Konstanz, Germany).

*H. Pylori* Culture Conditions

*H. pylori* cells were grown in liquid suspension in brain heart infusion medium (BHI, Difco). BHI medium was supplemented with 0.25% yeast extract (Difco) and 6% fetal calf serum (Eurobio). Cells were grown in a $CO_2$ incubator at 37° C. in 10 ml cell culture flasks. Growth was monitored by determination of the optical density at 578 nm and microscopy. Overnight cultures where cells were in log-phase growth were used for the experiments described below. For *H. pylori* transformation cells were grown under the conditions described in the corresponding experimental protocols.

Construction of a Plasmid Containing the KanR ORF Flanked by Partial Sequences of Ure B and Ure E A plasmid was constructed for subsequent exchange of the ureI open reading of the urease operon for a resistance marker gene in the genome of *Helicobacter pylori*. This plasmid should contain the coding of a resistance gene to be inserted into the *H. pylori* chromosome flanked by sequences for chromosomal targeting. As a resistance marker gene the open reading frame of a kanamycin gene cassette derived from plasmid pUC4K (Boehringer Mannheim) was used. The open reading frame of the resistance gene was linked to 3' terminal sequences from ureB (preceding kanR) and ureE (downstream of kanR) derived from the urease operon of *H. pylori*. In the urease operon, the ureI gene is located between ureB and ureE. Thus the kanR open reading frame contained in such a plasmid between the partial sequences of the ureI flanking regions of ureB and ureE should target the fusion sequences to the urease b/e sequences of the operon allowing homologous recombination. The result of this process was supposed to provide *H. pylori* mutants having a kanamycin open reading frame instead of ureI in the urease operon (ureAB-KanR-EFGH). Thus the resistance gene sequence, as part of the recombinant urease operon, is under control of the urease operon. Since this operon is constitutively expressed in *H. pylori*, this would allow selection of mutants in media supplemented with kanamycin.

For plasmid construction, a DNA primer carrying a Shine Dalgarno (SD) sequence was employed for amplification of the 5' region of the ureE gene via PCR. The same was done using the sequences preceding the ureI gene in the urease operon. Primers used for DNA amplification by PCR were linked to additional sequences introducing recognition sites of restriction enzymes for subsequent cloning. Sequences of primers used are given below. The PCR product of the partial ureB sequence were flanked by EcoR1 (5') and BamH1 (3') restriction sites while the partial ureE sequences was linked to recognition sites of Bam H1 (5') and a HindIII (3'). This procedure allowed fusion of the amplified ureB/ureE DNA via BamH1 compatible sequences and cloning of the fused PCR product using terminal EcoR1 and Hind III recognition sequences. The Bam H1 site of the hybrid fragment was used for insertion of the open reading frame of the pUC4K-derived open reading frame of the kanamycin gene. The latter sequence was amplified by PCR again using primers with terminal extensions carrying restriction sites. Restriction sequence used was the BamH1 reconition sequence allowing insertion of the amplified kanR DNA right between the ureB:ureE (BamH1) fusion point created as described above. The vector used here for cloning of the (EcoR1) partial ureB:kanR: partial ureE (Hind III) DNA fragment was pUC19 (Boehringer Mannheim). Plasmid was restricted with EcoR1 and Hind III for DNA fragment cloning. The generated plasmid containing the hybrid DNA fragment was transformed into *E.coli* DH5alpha (GATC, Konstanz) for plasmid replication. To select for the presence of the plasmid cells were grown in LB medium (LB broth base (Gibco BRL)) supplemented with 50 $\mu$g/ml ampicilin. Plasmids were assayed for presence and orientation of the insertional DNA employing restriction analysis. Plasmid DNA of this vector was used for homologous recombination in *H. pylori*.

Template DNA Employed for Polymerase Chain Reaction (PCR) for Subsequent Plasmid Construction As a template for the urease operon derived sequences one can use genomic DNA of *H. pylori* strains shown to contain an urease operon as a source for amplification of urease operon derived DNA. Examples of such strains are *H. pylori* ATCC49503, ATCC43504 or the strain used for *H. pylori* genome sequencing at TIGR (Tomb et al. (1997) Nature, 388, 539–547). The template used for PCR amplification of the ure B/E sequences described above was plasmid pHP808. DNA template for synthesis of the ORF of the kanamycin resistance gene (kanR) was pUC4K.

DNA Oligonucleotides

The primers were synthesized and HPLC purified by Interactiva (Ulm, Germany). The primers were diluted to a final concentration of 100 pmol/$\mu$l before employed for polymerase chain reaction (PCR). Sequences of primers used for construction of the plasmids described above were as followed:

5' gtc tac gaa ttc cgc tac ttg tct aaa tac (EcoR1/ureB primer; I-672),

5' gtc tac gga tcc cta gaa aat gct aaa gag ttg (BamH1/ure B primer I-700),

5' gtc tac gga tcc atg agc cat att caa cgg (BamH1/KanR, I-676)

5' gtc tac gga tcc tta gaa aaa ctc atc gag (BamH1/KanR, I-677)

5' gtc tac gga tcc agg aaa agg caa tga tca tag agc gtt ta (BamH1/ureE, I-674)

5' gtc tac aag cft ttt cat gac cac ttt aaa (Hind III/ureE, I-675)

Polymerase Chain Reaction (PCR)

For DNA amplification of sequences needed for plasmid construction PCR reactions were performed in a final volume of 50 $\mu$l using Pfu-polymerase (Stratagene). Amplification was carried employing standard protocols in a RoboCycler Gradient 40 (Stratagene) with varying annealing temperatures depending on the primers used (I-672/I-700: 53° C.; I-676/I-677: 56° C.; I-674/I-675: 51° C.). In each of the 25 cycles, DNA denaturation was done for 45 s at 95° C., annealing was for 45 s at the temperatures given above and polymerisation was for 3 min at 72° C., with an additional extension of 10 min of the polymerisation period after the last cycle. Reaction mixtures purified with PCR purification kit (Quigen). For subsequent cloning PCR products were restricted with appropriate enzymes.

Plasmid Isolation, DNA Purification and DNA Manipulation

Isolation of plasmid DNA and manipulation thereof (DNA restriction, DNA dephosphorylation, agarose gel electrophoresis, ligation) was performed using standard procedures (Ausubel et al. (ed) (1994) Current protocols in molecular biology, John Wiley & Sons, Inc., New York, N.Y.) The restricted DNA was purified with PCR purification kit (Qiagen), as was done for purification of DNA fragments obtained via PCR. Ligation was carried out at 16° C. for 16 hrs. Ligation enzyme used was T4 DNA-ligase (400 U/$\mu$l, New England Biolabs). Enzyme used for DNA dephosphorylation was shrimp alkaline phosphatase (SAP, Boehringer Mannheim). Purification of the plasmid DNA was done according to QlAprep Spin Miniprep Kit Protocol (Qiagen). DNA was eluted in 100 $\mu$l elution buffer (Qiagen).

DNA Transformation of *E.coli*

*E.coli* DH5alpha (GATC, Konstanz) was transformed via electroporation. A Gene Pulser II (BioRad) was used. Transformation was carried out according to a standard operation protocol using a 2.5 kV pulse. Immediately after electroporation 1 ml of SOC medium (SOB medium is 10 mM NaCl-2 mM KCl solution containing 20 g/L Bacto Tryptone and 5 g/L yeast extract; SOB medium supplemented with 20 mM sucrose, 10 mM $MgCl_2$ and 10 mM $MgSO_4$ is SOC medium) was added, and after 1 h of incubation at 37° C. electroporated cells were plated onto LB plates (LB agar base (Gibco BRL)) supplemented with 50 $\mu$g/ml ampicilin for growth and selection of transformed cells.

Transformation of Plasmid DNA Into *H. pylori* Cells

*H. pylori* was grown on brain heart infusion agar plates (Difco) supplemented with 10% horse serum (Gibco BRL) in gas pak jars under microaerophilic conditions (Anaerocult C, Merck) at 37° C. for 24 hours. Cells from one plate were harvested in 1 ml brain heart infusion broth (Difco) supplemented with 6% fetal calf serum (Eurobio). After determination of $OD_{578}$ the cells were diluted to give a final $OD_{578}$ of 0.1 (optical density at 578 nm). 1 ml of this suspension was incubated for 4–5 hours at 37° C. in 24 well plates in a incubator with 10% $CO_2$. After addition of the DNA the cell suspension was incubated for 24 hrs as mentioned above. The cultures were spread onto brain heart infusion agar plates for selection and growth as described below.

Selection of Kanamycin-Resistant *H. pylori* Strains Lacking UreI Gene

Selection of kanR *H. pylori* strains lacking ureI gene was done on brain heart infusion agar (Difco) plates supplemented with 10% horse serum (Gibco BRL) and 8 μg/ml kanamycin in gas pak jars under microaerophilic conditions (Anaerocult C, Merck) at 37° C. Colonies were spread on a quarter of a plate and incubated for another 2 days. To produce more cell mass the cells were plated again. To purify genomic DNA cells were harvested from one plate in 10 mM Tris/HCl pH 7.4, 1 mM EDTA, 10 mM NaCl. DNA was purified according to standard protocols (Ausubel et al. (ed) (1994) Current protocols in molecular biology, John Wiley & Sons, Inc., New York, N.Y.).

Characterization of Mutated *H. pylori* Strains by PCR, Western Blot Analysis and Urease Activity

PCR

To assay genomic DNA of the selected clones for presence or absence of the kanamycin resistance ORF or that of the ureI gene, PCR was carried out using the following primers:

5' gtc tac gaa ttc cgc tac ttg tct aaa tac (ureB, I-672)
5' gtc tac aag ctt ttt cat gac cac ttt aaa (ureE, I-675)

PCR was carried out as described above but using a modified cycling program. 25 cycles were carried out after 1 min at 95° C. for initial DNA denaturation consisting of 45 s at 95° C., 45 s at 51° C. and 2 min at 72° C., with an extension of 10 min at 72° C. after the last cycle. Since the resulting product does not significantly differ between the wild type situation and the corresponding kanR-modified sequence of ureI knock-out mutants substituting the UreI coding region and 5' preceding sequences of the rel ORF which are noncoding (ca. 1800 bp vs ca. 1845 bp), an additional PCR reaction was performed to demonstrate the absence of ureI in the mutants. DNA primers employed were 5' atg cta gga ctt gta ttg fta (I-722) and 5' tca cac cca gtg ttg gat (I-723). After initial denaturation of the probes PCR cycling was carried out for 45 s at 95° C., followed by 45 s at 42° C. and 2 min at 72° C. (25 cycles), again with an final extension of 10 min at 72° C. All PCR products were analyzed by gel electrophoresis using standard procedures.

Western Blot Analysis

Protein concentration was determined according to Bradford (Bradford M. (1976) Anal. Biochem, 72: 248–252). 1 μg of proteins were separated onto 10% SDS polyacrylamide gels under reducing conditions (Laemmli U.K. (1970) Nature, 227:680–685). After electrophoresis, the proteins were stained with silver (Heukeshoven, J. and Dernick, R. (1985) Electrophoresis, 6:103–112) or Western blotted onto Protran nitrocellulose membrane (Schleicher & Schuell) using TransBlot apparatus from BioRad. The presence or absence of urease subunit B was demonstrated by incubation of the membranes with antiserum SE744 (α-UreB) raised again the β subunit of the *H. pylori* urease enzyme. Bound antibodies were detected by chemiluminescence using ECL system (Amersham).

Identification and Determination of Urease Activity (1) Rapid Urease Test

This procedures allows rapid but qualitative identification of urease activity. Just to assay whether a bacterial strain is urease positive or negative aliquots of bacterial material was mixed with 60 μl 0.02% cresolred (Merck), 0.1% EDTA. After addition of 30 μl of a 1.5% urea solution the reaction mixtures turned from yellow into a deep purple color within a few minutes, if the strain is urease positive.

(2) Determination of Ammonia Production

For preparation of bacterial extracts parental *H. pylori* cells as well as corresponding ureI-knockout mutants were grown in brain heart infusion broth (BHI, Difco) supplemented with 6% fetal calf serum (Eurobio), 0.25% yeast extract (Difco) and 8 μg/ml kanamycin for the knockout strain carrying the kanamycin cassette in gas pak jars under microaerophilic conditions (Anaerocult C, Merck) at 37° C. and 120 rpm. 10 ml bacteria were harvested by centrifugation at 4000 rpm (Z360K, Hermle, Gosheim, Germany) and stored at −20° C. For further experimental analysis the pellet obtained from 10 ml bacterial suspension was resuspended in 300 μl 50 mM phosphate buffer pH 6.8 and lysed by freeze and thaw. Extracts were prepared by centrifugation (16000 rpm, 4° C., 15 min) using SS34 rotor and supernatants were stored on ice. 20 μl of extract was added to 1 ml of 50 mM phosphate buffer pH 6.8. To start reaction 20 μl of 1.25 M urea was added. Samples for endpoint determination were taken after 2, 4, 6 and 8 min e.g. by transferring 20 μl aliquots of the reaction mixtures to 2 ml $H_2O$. Immediately after taken the samples 1 ml 2% sodium phenolate (Merck), 0.5 ml sodium nitroprusside (Sigma, 50 mg/ml) and 0.5 ml NaOH solution (dissolve 1 g NaOH in 20 ml sodium hypochloride and add $H_2O$ bidest to 200 ml) were added. $NH_4^+$ was determined colorimetric by measuring the absorption at 660 nm after 60 minutes of incubation at 37° C. Protein determination: Protein concentration of bacterial extracts was determined according to Bradford (Bradford, M. (1976) Anal. Biochem, 72: 248–252).

(3) Determination of $CO_2$ Production

Another method employed for quantitative measurement of urease activity was release of radioactive $CO_2$ form 14C-urea. The incubation medium contained 5 mmol/L labeled urea with a specific activity of 10 μCi/μmol. In the experiments reported, we used 100 mM sodium phosphate buffer at the required pH over a range of 2.5–8.5 in balanced salt solution (138 mM NaCl, 5 mM KCl, 1 mM CaCl, 0.5 mM MgCl2, 10 mM glucose and 1 mM glutamine). The pH was adjusted with NaOH or HCl. Details of the experimental procedure used is reported by Scott et al. (Gastroenterol (1998) 114, 58–70). Radioactivity of released $CO_2$ of cleaved urea was counted in a LKB scintillation counter (Wallac, Gaithersburg, Md., USA). Protein was determined by Lowry et al. (J Biol Chem (1951) 193, 265–275).

Cytosensor Experiments

The cytosensor microphysiometer provides a perfusion system allowing real time determination of the metabolic activity of small populations of living cells. The design and use of this instrument (Molecular devices Corp., Sunnyvale, USA) is described in details elsewhere (Owicki & Parce (1992) Biosensors Bioelectronics 7, 255–272; Hafeman et al. (1988) Science 240, 1182–1185; Parce et al. (1989) Science 246, 243–247; McConnell et al. (1992) Science 257, 1906–1912). Briefly, this machine allows measurement of the rate at which cells acidify or alkalinize the perfusion medium simultaneously in 8 sensor chambers. In these chambers the cells are in close contact via aqueous diffusion with a light addressable potentiometric pH sensor. The primary sensor output is in voltage (mV; raw data) and the change of voltage per unit time (μV/s; rate data) is calculated by a computer. Medium perfusion is controlled by a peristaltic pump. The pump cycle is periodically interrupted by flow off for determination of the metabolic rates (rate measurements in given in μV/s). The microphysiometer experiments were run with *H. pylori* entrapped in the chambers by using agarose cell entrapment medium (Molecular devices Corp., Sunnyvale, USA).

These protocols disclosed below allow to monitor the metabolic and urease responses of *H. pylori* cell populations under acute acid exposure or under a gradually changing pH of the perfusion medium. They further allow determination of recovery rates of metabolism after acidic challenge. It is also possible to calculate the effects of bacterial metabolism and urease activity on the steady state pH of the perfusion medium. The use of these protocols provides a means to measure pH-dependent changes of urease enzyme activity and the effects of urease activity and perfusion medium pH on the metabolic activity on *H. pylori*. Therefore these protocols are a convenient means for analysis whether genetic defects of *H. pylori* relate to acid resistance or pH-dependence of urease activity. The design of the experiments performed here, the pump cycle employed and the calculation of urea as well as pH-dependent effects are described in detail herein. The balanced salt medium used here was termed BSSGG.

Cytosensor Microphysiometer

Microanalysis of the production of $H^+$ or $OH^-$ by *H. pylori* was performed using a cytosensor (Molecular Devices Corp., Sunnyvale, USA). This machine reports the effects of cells retained in microflow chambers on the pH of the perfusing medium. Cells are in aqueous diffusive contact with a light addressable potentiometric pH sensor (LAPS). The cytosensor consists of 8 flow sensor chambers and associated components managed by one computer. It allows measurement of the rate at which cells acidify or alkalinize the medium simultaneously in these 8 chambers. As mentioned above, primary sensor output is in voltage (mV) and the change of voltage ($\mu V$) per unit time (sec) is calculated by the computer. This is proportional to rate of change of $H^+$ concentration in the medium. Rates of acidification or alkalinization are determined during periodic interruptions of the flow of the medium (rate measurements). Net effects of bacterial metabolism and urease activity on the steady state pH in the microflow chamber are calculated by comparing the raw data mV readout from control chambers which did not contain *H. pylori* cells (inflow pH) to pH of the perfusion medium after passage through the microflow chamber retaining *H. pylori* cells (outflow pH).

Preparation of Cells and Microphysiometer Analysis

Cytosensor experiments were run with *H. pylori* immobilized in microvolume flow chambers in close contact with the pH sensitive silicon LAPS sensor according to the manufacturer's manual. Cells were immobilized by using agarose cell entrapment medium (Molecular devices Corp., Sunnyvale, USA). Approximately $1-5 \times 10^5$ bacterial cells were trapped between two microporous membranes and loaded into each of the sensor chambers. These were perfused with balanced salt solution (BSS: 138 mM NaCl, 5 mM KCl, 0.81 mM $NaH_2PO_4$, 1.3 mM $CaCl_2$, 0.5 mM $MgCl_2$, pH 7.4) supplemented with 10 mM glucose and 1 mM glutamine (BSSGG) at 37° C. When experiments were run under varying pH values BSSGG was adjusted to the pH desired by addition of HCl. These media lacking complex extracts and blood serum did not allow growth of *H. pylori* during incubation in the sensor chambers of the microphysiometer. Thus the metabolic activities of bacterial populations, as detected by means of Cytosensor analysis described below, are net effects of *H. pylori* metabolism not influenced by stimulation or inhibition of bacterial growth.

Pump Cycle and Flow Rate

The 1 min pump cycle (total time) used was 40 s for the pump interval (seconds 0–40) followed by a break of 2 s, then an interval of 16 s for rate measurement and a break of 2 s before the start of the next cycle. The flow rate was set at 400 $\mu$l per minute.

Cytosensor Data Collection

The cytosensor monitored and displayed the collected activities of living cells in two configurations termed raw and rate data. Raw data collected every second during the entire experiment were displayed in mV. The rate data were calculated every minute from the slope measurements recorded during the pump off period. Rate data are recorded and displayed in $\pm \mu V/sec$. Raw data plots showed that bacterial populations acidify the BSSGG medium at pH 7.4 during the pump off period (voltage drop) and that the acid is washed out by medium flow during the following pump on period (voltage rise). When the medium is supplemented with urea the cytosensor now is able to detect a net alkalinization of the medium during the pump off periods when the urease-positive *H. pylori* strain are retained in the pH-sensitive microphysiometer chambers (voltage increase) and, in turn, medium pH returns to more acidic baseline levels during flow on perios (voltage decrease). During each flow off period, the slope of the sensor raw data is automatically calculated by a least-squares procedure and reported as rate of medium acidification or alkalinization. The rate data are displayed in $\mu V\ sec^{-1}$ where $1\ \mu V\ sec^{-1}$ is close to $1 \times 10^{-3}$ pH units per minute.

Experimental Design

Before running an experiment, the cytosensor with loaded sensor chambers was calibrated as described in the manual provided by the manufacturer. After calibration, in each experiment, the acidification rate due to *H. pylori* metabolic activity was initially recorded in BSSGG medium at pH 7.4 for determination of the metabolism at neutral pH using the pump cycle described above. After stabilization of acidification rates, the valve position was changed to alter perfusate composition. After exposure to a different pH, urea or inhibitors for the times indicated in the experiments described in results (experimental examples), another valve position change was performed so that the cells were exposed to initial medium, BSSGG pH 7.4, allowing determination of the recovery of acidification rate. The pH in the gastric lumen undergoes either gradual or sharp changes in pH, perhaps also reflected as gradual or sudden pH changes on the gastric surface. The experiments in the physiometer attempted to mimic gastric conditions. Various types of experiments were run with changes of input pH without or with urea. Two sets of experiments determined the rate of acidification or alkalinization while the pump was stopped taking advantage of the high sensitivity of the instrument. One set consisted of initial perfusion at input pH 7.4 with then step down or up to the final pH and then restoration to pH 7.4. This allowed measurement of metabolism at the given pH and of the ability of the organism to recover its metabolism after sudden exposure (also termed as acute acid exposure) to different medium pH. A second type of experiment consisted of a gradual stepwise reduction of medium pH down to a final pH of 2.5 (with 2.5 mM urea) allowing adaptation to medium pH prior to the measurement of metabolism or recovery from acid exposure. The input pH ranged from 2.5 to 7.4 in these experiments.

Growth of *H. pylori* After Acidic Challenge

Growth Media and Buffers

The buffers used were as follows: phosphate buffer consisting of 5 mM KCl, 138 mM NaCl, 1.3 mM $CaCl_2$, 0.5 mM $MgCl_2$, 10 mM glucose (pH 7.0), 0.11 mM $NaH_2PO_4$, and 0.81 mM $Na_2HPO_4$ (weak buffering capacity); citrate phosphate buffer consisting of 138 mM NaCl, 5 mM KCl, 1.3 mM $CaCl_2$, 0.5 mM $MgCl_2$, 100 mM citric acid-$Na_2HPO_4$ by mixing 0.1 M citric acid with 0.2 M $Na_2HPO_4$ until the desired pH (pH 2.0 and 3.0) was reached (strong buffering capacity) or 100 mM Tris(HCl) pH 7.0 supplemented with the salts described above (strong buffering capacity).

*H. pylori* was grown on brain heart infusion (Difco) agar plates supplemented with 10% horse serum (Gibco BRL) in gas pak jars under microaerophilic conditions (Anaerocult C, Merck) at 37° C. for 24 hours. For growth of mutants lacking the ureI gene agar plates were supplemented with 8 μg/ml kanamycin. Cells from one plate were harvested in 300 μl phosphate buffer pH 7. from which aliquots were taken for the incubation experiments. 5 μl of the bacterial suspension was added to 1 ml of the 100 mM citrate phosphate buffer of the pH 2.0 or pH 3.0 in the presence or absence of urea (5 mM or 10 mM). Citric acid buffer was prepared via mixing 100 mM citric acid with 0.2 mM $Na_2HPO_4$ until the desired pH was reached. As controls, bacteria were also added to 100 mM Tris(HCl) pH 7.0 supplemented with salts. The samples were incubated at 37° C. under microaerophilic conditions (5% $O_2$, 10% $CO_2$, and 85% $N_2$) using a gastight, evacuable jar (Oxoid) in the presence or absence of 10 mM urea. After 30 min of incubation 40 μl samples were suspended in 1 ml brain heart infusion broth (Difco) supplemented with 6% fetal calf serum (Eurobio) and 0.25% yeast (Dicfo) ±8 μg/ml kanamycin for recultivation to see the effects of incubation at different pHs. Bacteria were incubated under microaerophilic conditions (Anaerocult C, Merck) as mentioned above in a shaker incubator at 37° C. Optical density of bacterial solutions were measured at 578 nm after a period of 21, 28 and 48 hours using a spectrophotometer.

pH-Shift-Assay

Unbuffered solutions were 140 mM NaCl, 2.5 mM KCl adjusted with HCl to a final pH of 2.0 or 4.0. *H. pylori* cells were grown in liquid culture under standard conditions, as described above. Cells were harvested by centrifugation for 15 min at 3000 rpm in a Hermle Z360K centrifuge (Hermle, Gosheim, Germany). The supernatant was removed carefully and the pellet was resuspended in the appropriate unbuffered solution (pH 2.0 or 4.0) ±10 mM urea to an final OD 578 of 1.0. The pH of the supernatant was measured with pH-meter 766 Calimatic (Knick, Berlin).

Examples of Results Obtained with the Procedures and Assays of UreI-Dependent Helicobacter Acid Resistance Here data obtained by employing experimental procedures (as described above) to analyze ureI-dependent mechanism of *H. pylori* acid resistance are described. It is shown that these procedures are well able to detect these mechanisms and therefore these methods are well appropriate for detection of substance interaction with the above mechanisms of gastric Helicobacter.

Generation of UreI-Deficient Mutants

*H. pylori* mutants with the ORF of kanamycin instead of ureI were obtained using the cloning procedure described in above. Knock-out mutants were obtained after plasmid transformation and kanamycin selection from *H. pylori* 69A as well as from the other parental strains used in this study, namely ATCC49503, ATCC 43504 and *H. pylori* strain P49, respectively. PCR analyses demonstrated presence of the kanamycin gene and absence of the ureI gene. Generation of the mutants indicated that the promoter-less kanamycin gene is expressed from the urease promotor as part of the urease operon. A schematic presentation of the wild-type urease operon and the modified operon constructed with the ORF of a kanamycin resistance gene instead of the ureI ORF is depicted in FIG. 1.

Cell populations from distinct kanamycin-resistant colonies obtained after plasmid transformation of the different parental strains were qualitatively assayed for urease activity using the kresolred assay. All ureI Knock-out-mutants were able to alkalinize the medium, as did the corresponding wild-type strains. Next Western blot analysis was employed using an anti UreB antibody raised against the *H. pylori* UreB subunit of the urease enzyme. The antibody detected the ureB protein in all ureI-deficient mutants and their corresponding wild-type cells. An example is given in FIG. 2. To further check for the specific enzyme activity expressed in *H. pylori* wild-type cells and their corresponding mutant, of *H. pylori* 69A and the ureI-deficient mutant derived from *H. pylori* 69 were prepared and enzyme activity was determined. Compared to the wild type strain *H. pylori* 69A the ureI-knock out mutant did not show significant lower urease activity. Typically such an analysis provides urease activities of about 15–20 enzyme units given in μmol $NH_4$+/min×mg protein for both wild-type cells and mutants. Thus the results obtained for the mutant and the wild-type strain were nearly identical.

These data demonstrated that active urease is expressed in ureI-deficient mutants to wild-type levels and that we were not able to detect differences between the ureI knock-out mutants and the corresponding wild-type cells using the assays described above.

Profile of Urease Activity in Strong Buffers

As mentioned above, there was no significant difference detectable in both urease enzyme expression and activity. Next the profile of urease activity of intact bacteria (ureI knock-outs and wild-type cells) in strong buffer of various medium pH was analyzed. The results are shown in FIG. 3. Comparing the two distinct cell populations it can be seen that bacterial urease enzyme activity was nearly identical at pH 7.0. At pH 6.0 and below bacterial urease activity of the wild-type strain increased and was observed down to pH 3.0 in this type of experiment, as expected for activity of the urease enzyme of *H. pylori*. In sharp contrast, the corresponding ureI-deficient mutant was not able to activate the enzyme by exposure to acid. Urease activity was significantly deceased at pH 6.0 and was absent at pH 5.0 and below.

There are additional possibilities to monitor urease activity, as for example the use of pH-sensitive fluorescent dyes.

Profile of Urease Activity by Perfusion in Lightly Buffered Media

To measure the effect of external pH on *H. pylori* urease activity in the presence and absence of ureI gene expression the Cytosensor microphysiometer was used. The use of this equipment for analysis of *H. pylori* metabolism and urease activity under both conditions of acute acid exposure or exposure to gradual falling medium pH to allow pH-adaption of bacterial population have been described in detail herein.

Acute Acid Exposure

*H. pylori* cell population acidified the medium pH of the microphysiometer chamber under in stop flow periods (rate data measurements) in the absence of urea at pH 7.4, as described herein. Here experiments first performed with *H. pylori* 69A and its ureI-deficient derivative where cell populations acidifying at pH 7.4 were challenged to acidic media containing 2.5 mM urea for 30 min are described. These media were adjusted to pH 5.0, 4.0, 3.5, 3.0 or 2.5. When *H. pylori* 69A wild-type cells initially perfused at pH 7.4 were challenged to pH 5.0 medium supplemented with 2.5 mM urea, medium alkalinization occurred during rate measurements at a rate of about −500 to −800 μV/s. Rates of alkalinization were between −3000 to −4000 μV/s at pH 4.0, around −10000 μV/s at pH 3.5 and <−500 μV/s at pH 3.0 and 2.5. Use of the ureI knock-out mutant gave significantly different results in media of pH 3.0 and below. Presence of the mutant in the microphysiometer chamber also led to medium alkalinization rates around −500 through −800 μV/s at pH 5.0 when medium supplemented with 2.5 mM urea and preadjusted to pH 5.0 was used for perfusion. At medium pH 4.0 there was an increase of alkalinization during stop flow to about $-2000$ $\mu$V/s. In contrast to wild-type cells, the alkalinization rates measured with the ureI mutant was only around $-200$ $\mu$V/s at pH 3.5 and less than the former value at pH 3.0 and 2.5. Results are shown in FIG. 4.

Figure 5:
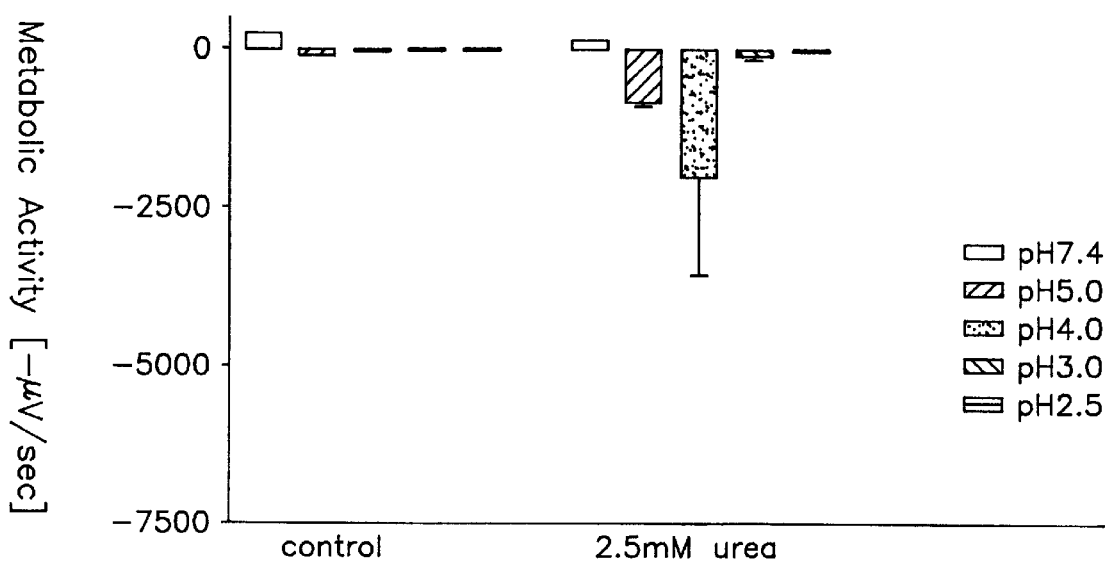
FIG. 5 illustrates alkalinization rates of ureI knock-out cells of *H. pylori* ATCC 49503 measured in a microphysiometer under acute acid exposure.
Figure 6:
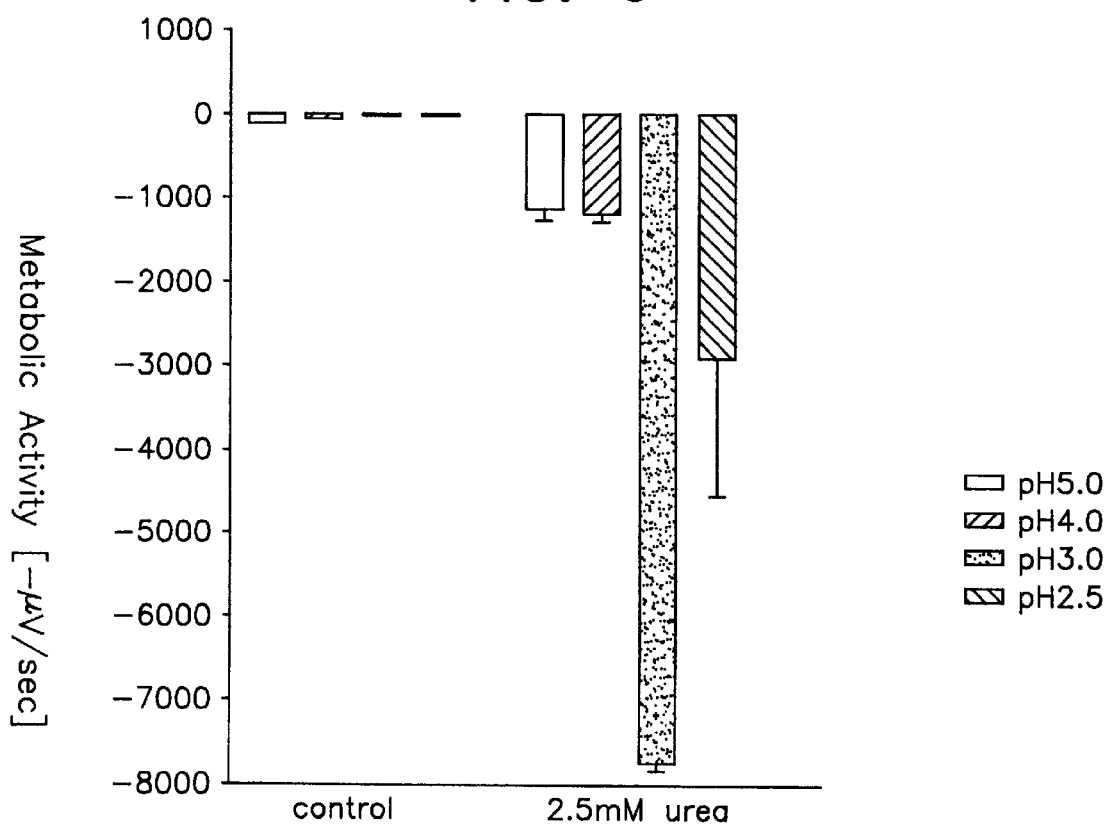
FIG. 6 illustrates alkalinization rates of *H. pylori* ATCC 49503 lacking ureI gene in a microphysiometer under acute acid exposure.

In a former study we have investigated the effect of medium pH on the rates of alkalinization of *H. pylori* ATCC49503. The data obtained showed that this strain has the strongest rate of medium alkalinization (around $-8000$ $\mu$V/s) at medium pH 3.0 (Scott et al, in *H. pylori*: Basic mechanisms to clinical cure 1998 (eds. Hunt et al) Kluwer Academic Press, London 1998; p. 133–147). When the ureI knockout mutant of *H. pylori* ATCC49503 were challenged to acute acid exposure, rates of medium alkalinization was about $-200$ $\mu$V/s at pH 3.0 and even absent at pH 2.5 (FIG. 5). ATCC49503 alkalinized the medium at rates of about $-8000$ $\mu$V/s at medium pH 3.0 and $-3000$ $\mu$V/s at pH 2.5 (FIG. 6). The results show that stimulation of urease activity is even present in the ureI mutants but activation of the enzyme is restricted to the pH range of moderate activity. Strinkingly, the dramatic increase of urease-mediated medium alkalinization, as observed at pH 3.5 for *H. pylori* 69A and at pH 3.0 for *H. pylori* ATCC49503, was absent in the ureI mutants. These data also show that there were slight differences in the pattern of pH stimulation of distinct *H. pylori* strains. However, ureI expression is essential for urease activity of *H. pylori* cells in media of high acidity.

Figure 4:
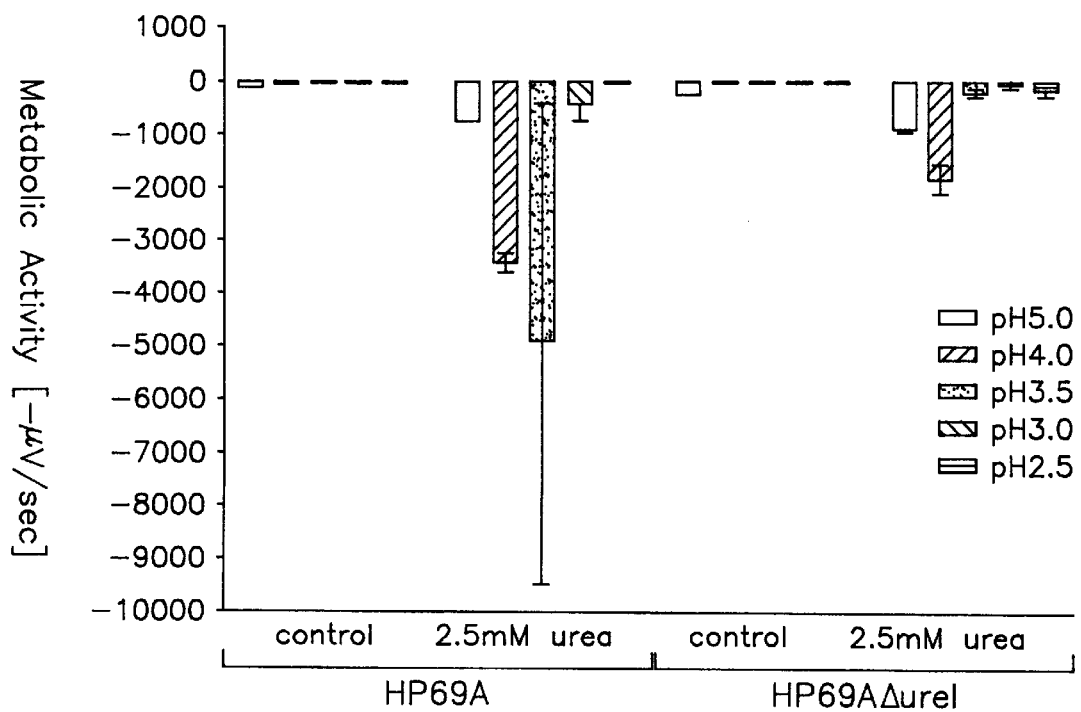
FIG. 4 illustrates alkalinization rates of *H. pylori* 69A and corresponding mutant lacking ureI measured in a microphysiometer under acute acid exposure.

The strong alkalinization rates obtained in this type of experiment is dependent on the presence of urea in the medium, as demonstrated by the lack of significant alkalinization rates detected when cells were perfused with acidic media without urea (see controls in FIG. 4–6).

The recovery rates of metabolism were monitored by switching back the medium pH to pH 7.4 (the initial medium pH before pH challenge) and determining the metabolic activity at this neutral perfusion pH. Recovery data are described in a separate paragraph.

Perfusion With Media of Increasing Acidity

Figure 7:
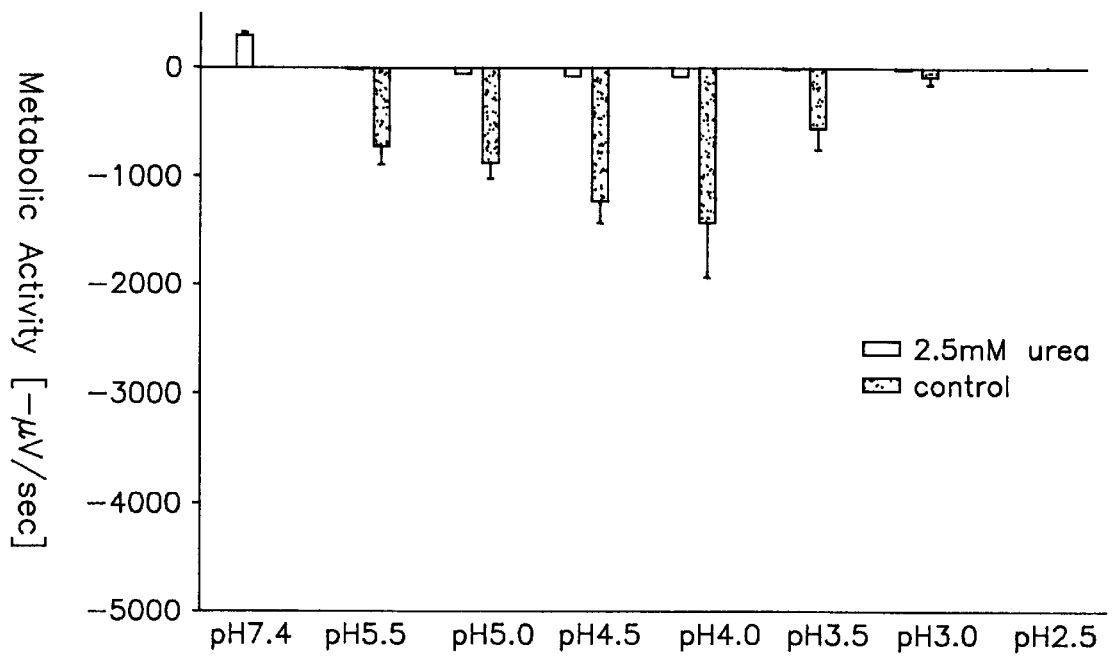
FIG. 7 illustrates rates of medium alkalinization of acid-adapted *H. pylori* 69A ureI mutant in a microphysiometer during exposure to media of gradually increasing profusion pH.
Figure 8:
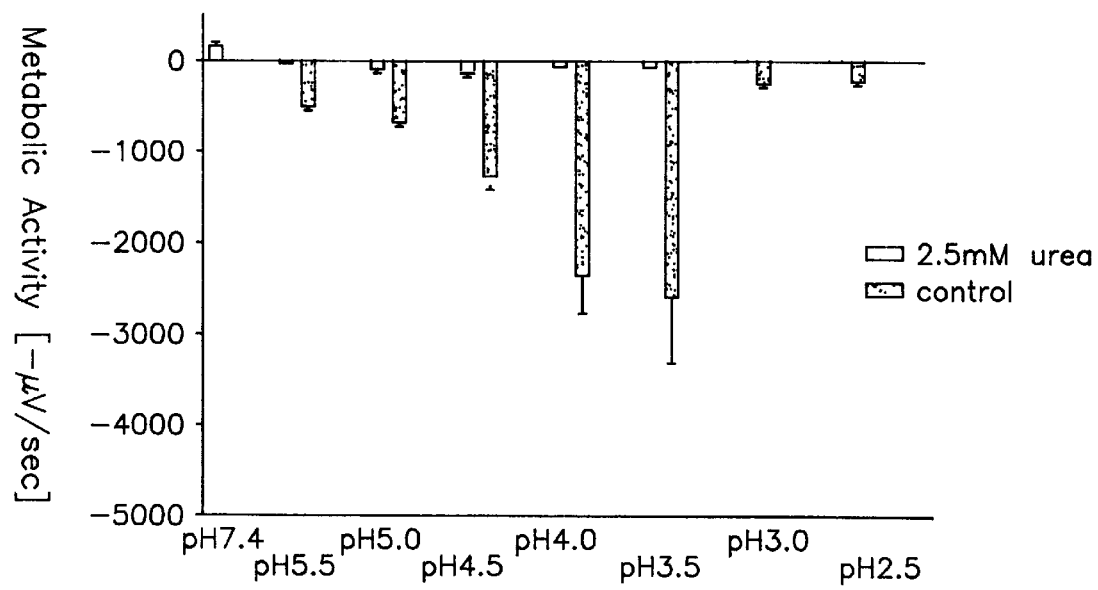
FIG. 8 illustrates rates of medium alkalinization of pH-adapted *H. pylori* 69A in a microphysiometer during exposure to media of gradually increasing profusion pH.

In contrast to acute acid exposure, in this type of experiment cell populations were challenged to media of stepwise decreasing medium pH. Initial medium pH was set to 7.4. Stepwise medium pH gradient was pH 5.5, 5.0, 4.5, 4.0, 3.5, 3.0, 2.5. Cells were perfused at each medium pH for 30 min. This protocol allowed the cells to adapt to medium acidity. In FIG. 7 and FIG. 8 the mean values of bacterial alkalinization, as obtained during 30 min perfusion for each medium pH, were calculated. FIG. 7 summarized the results we have obtained by employing the *H. pylori* 69A ureI⁻ derivative. In the absence of urea, cell populations of this strain acidified the medium at pH 7.4. When the medium pH was decreased to 5.5 the mutant alkalinized the medium at a rate of about $-800$ $\mu$V/s. This rate increased stepwise up to about $-1500$ $\mu$V/s during gradual fall of perfusion pH down to pH 4.0. Alkalinization rates then decreased at pH 3.5 and were nearly absent at pH 3.0 and 2.5 in these experiments with the *H. pylori* 69A mutant. The wild-type *H. pylori* 69A strain gave similar alkalinization rates at pH 5.5, 5.0 and 4.5 (FIG. 8). In contrast to the ureI knock-out mutant, *H. pylori* 69A demonstrated elevated rates of medium alkalinization when the cells were perfused with medium of pH 4.0 and pH 3.5 (between $-2000$ through $-3000$ $\mu$V/s) indicating increase of urease enzyme activity. Alkalinization rates felt below $-500$ $\mu$V/s at pH 3.0 and 2.5. As can be seen by comparison of FIGS. 7 and 8 the results show that, with respect to urea-dependent medium alkalinization, there was no significant difference between wild-type *H. pylori* 69A and its mutant in the range of moderate perfusion medium acidity. Stimulation of medium alkalinization was observed in both strains. In the media of higher acidity the ureI-deficient mutant did not maintain strong medium alkalinization (pH 3.5) and alkalinization was more or less absent at low pH (pH 3.0 or less).

In conclusion from these results obtained with the ureI knock-out mutant acid stimulated medium alkalinization is dependent on ureI during perfusion of bacteria with media of higher acidity. This dependency was shown to occur in both, pH-adapted *H. pylori* cells as well as *H. pylori* cell populations which are pre-exposed to moderate medium acidity before challenged to medium of high acidity. We also analyzed whether the ureI gene affect the metabolic survival of the gastric bacterium during gradual acid exposure by determining the recovery rates of medium acidification.

Recovery Rates of Metabolism After Acid Exposure

The role of ureI gene expression for maintenance of *H. pylori* metabolism in an acidic environments by employing *H. pylori* mutants lacking the ureI gene in the urease operon but expressing functional urease enzyme was analyzed. Metabolism is necessary for bacterial survival. In the experiments described below we demonstrate that maintenance of *H. pylori* metabolism in media of higher acidity essentially depends on ureI, as does maintenance of strong medium alkalinization (see above).

In a detailed study using a perfusion microphysiometer we have shown that *H. pylori* has the capacity to maintain its metabolism (measured as medium acidification due to bacterial metabolism) even when exposed to media of strong acidity. It was shown that maintenance of metabolism in acid and, therefore, metabolic recovery after acidic challenge depends on the presence of urea in the medium and an active, pH-dependent urease enzyme. In addition, bacterial pH-adaptation also plays a role (Scott et al, in *H. pylori*: Basic mechanisms to clinical cure 1998 (eds. Hunt et al) Kluwer Academic Press, London 1998; p. 133–147). These features of *H. pylori* must be considered as prerequisite for survival in a gastric environment.

Recovery Rates After Acute Exposure to Acid

We first studied how the absence of the ureI gene affects the recovery rates of metabolism during acute acid exposure (that is use of *H. pylori* cell populations which are not pre-adapted to acid exposure). Cells were exposed to media of different pH for 30 min. Media were supplemented with 2.5 mM urea. Controls were perfused with media without urea. pH of the perfusion medium was set back to the initial pH after pH challenge and metabolism was measured at pH 7.4. In the absence of urea in the media there was a pH-dependent decrease of recovery observed for both *H. pylori* 69A and the corresponding ureI knock-out strain. Only low recovery rates or even absence of metabolic activity was observed after exposure to media to <pH 4.0. pH-dependent decrease of metabolic recovery was accelerated to some extend in the ureI mutant. However presence of 2.5 mM urea enabled metabolic survival of *H. pylori* 69A during acidic perfusion. Recovery rate of acidification after pH 3.0 or pH 2.5 exposure for 30 min was between 80–100% of the initial acidification rate (the initial rate determined before acid perfusion was set to 100%). The mutant also showed elevated rates of metabolic recovery when the medium contained 2.5 mM urea. Recovery was around 60–80% after pH 3.5 and pH 3.0 perfusion. There was a drop in recovery rates after 30 min exposure to pH 2.5 medium to about 40% of the initial acidification rate.

Figure 10:
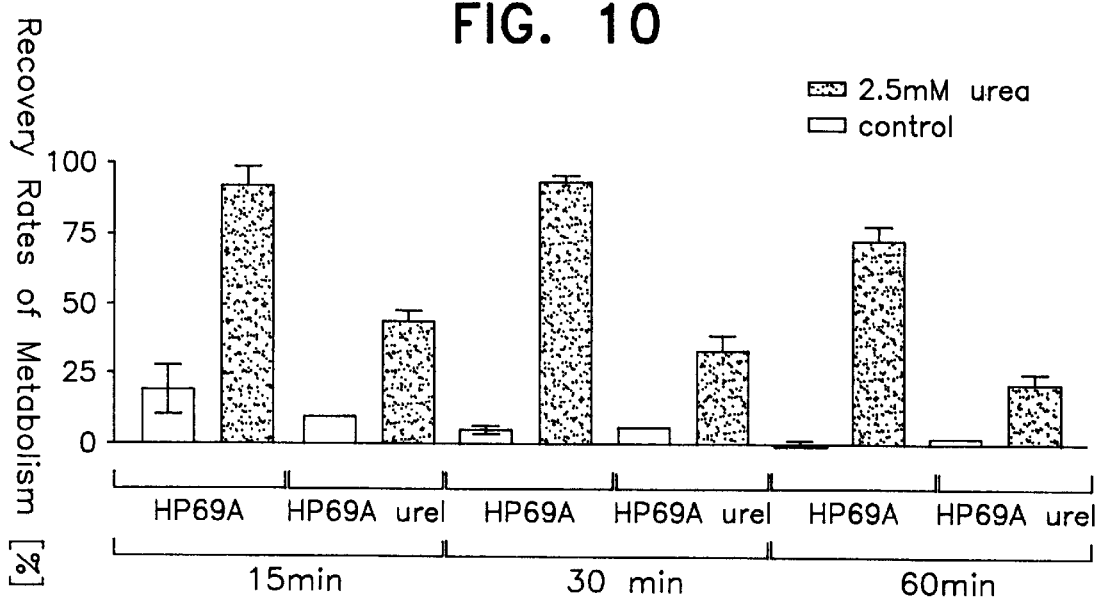
FIG. 10 illustrates recovery rates of acidification at pH 7.4 after acute acid exposure of *H. pylori* 69A and ureI-lacking derivative.

The above result indicates that the ureI knock-out mutant showed a decrease in the ability to maintain the metabolism in low pH media. Thus we analyzed whether there is a time dependency of the effect of pH 2.5 exposure on metabolic recovery of the ureI-deficient mutant using the parental strain as a control. In these experiments cells were perfused at pH 2.5 for 15, 30 and 60 min (FIG. 10). The results demonstrate that the absense of the ureI gene led to decrease rates of metabolic resistance in the mutants and that longer exposure to acid resulted in accelerated inhibition of metabolism in these experiments of acute acid exposure.

Recovery Rates after Exposure Gradually Decreasing Medium pH

Compared to the conditions used for acute acid exposure, two important differences emerged in the type of experiment where cells were exposed to a gradual fall of medium pH. These differences have to be considered for data interpretation. First of all cells before reaching the final acidic medium pH of 2.5 were challenged to a stepwise fall of perfusion pH also covering the range of moderate acidity where pH-adaptation can occur. Secondly, here in these experiments which last about 4 hours acid exposure is for hours. The ability of H. pylori to retain metabolism during this long-termed pH challenge was determined after acid perfusion at pH 7.4, as was done in the experiments of acute acid exposure.

Figure 9:
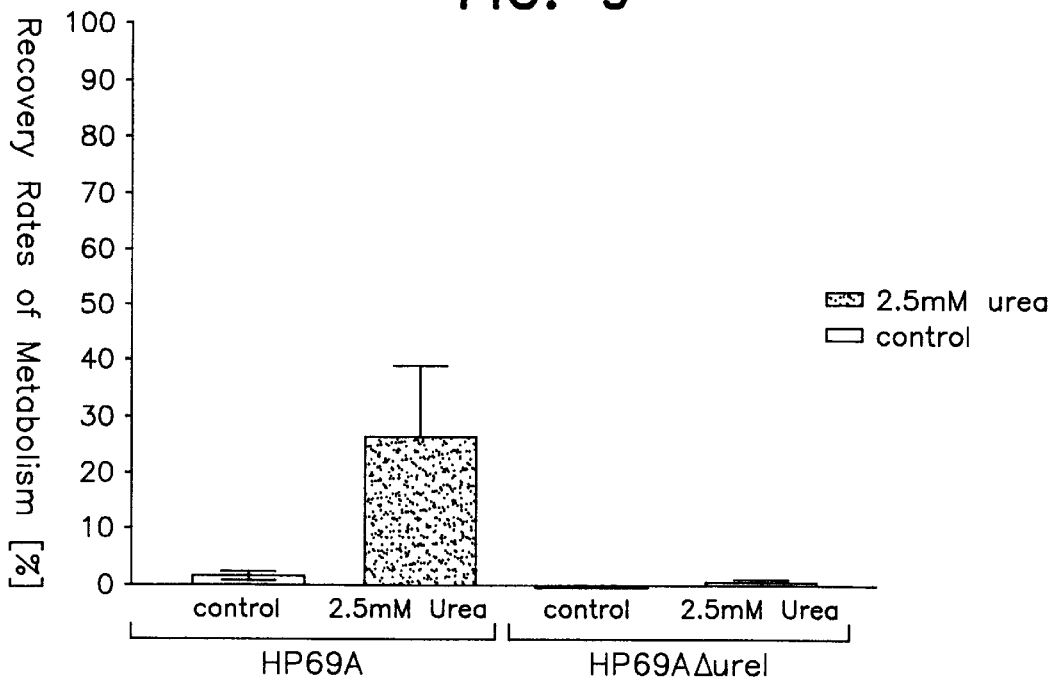
FIG. 9 illustrates recovery rates of medium acidification of *H. pylori* 69A and the corresponding ureI knock-out strain after exposure to gradually decreasing profusion pH.

Results obtained with H. pylori 69A and its ureI-deficient derivative are presented in FIG. 9. Wild-type cells revealed recovery rates of acidification of about 30% essentially depending on the presence of urea in the medium. In contrast, the mutant was not able to recover metabolism even during acid exposure using media containing 2.5 mM urea. The same pattern of metabolic survival was found for other strains (data not shown). For example, H. pylori ATCC49503 showed recovery rates of metabolism around 50% after the final pH 2.5 challenge (2.5 mM urea) and even in the presence of only 0.1 mM urea metabolic recovery of about 25% have been observed. In contrast, replacement of the ureI ORF in the genome of H. pylori ATCC49503 for the ORF of a kanamycin resistance cassette resulted in the loss of these capacities. Metabolic recovery could not be detected when the latter mutant was used (data not shown). In summary, metabolic survival of H. pylori essentially is dependent on the ureI gene when cells (even pH-adapted) were exposed to pH 2.5.

Examples for Assays Based on a Process According to the Invention

Effect of Wild-Type H. pylori Cells and UreI-Deficient Mutant on Medium pH (pH Shift Assay)

Figure 11:
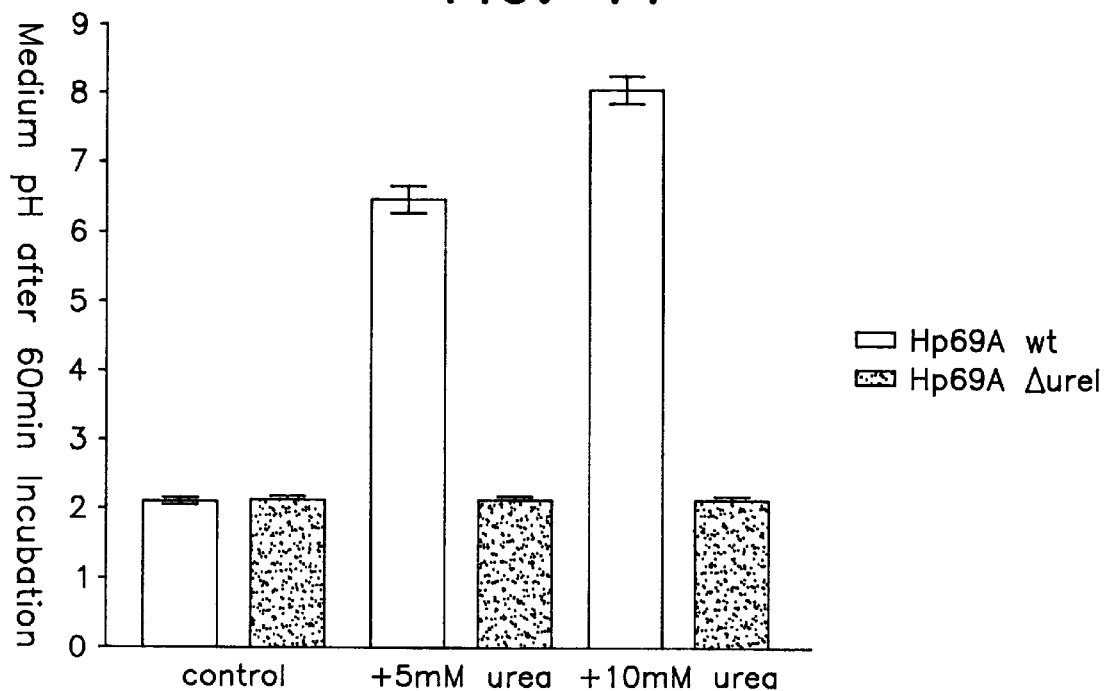
FIG. 11 reflects a pH shift assay showing the effect of *H. pylori* on acidic incubation pH in the presence or absence of ureI gene (initial pH 2.0).
Figure 12:
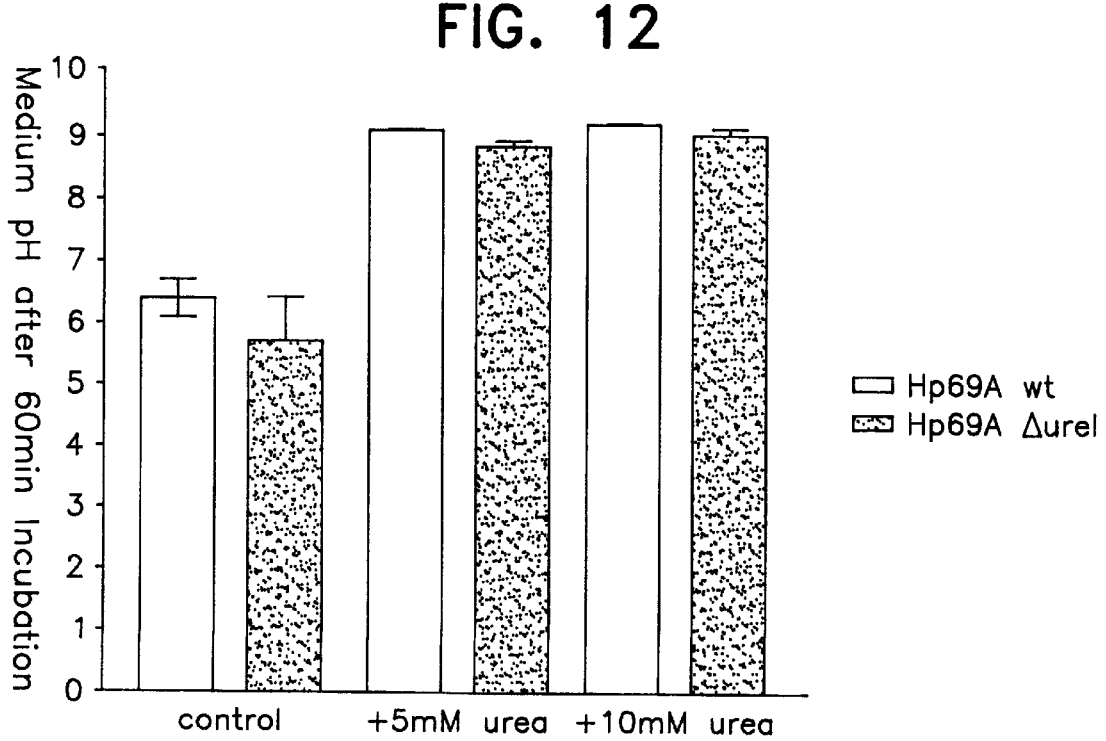
FIG. 12 reflects a pH shift assay showing the effect of *H. pylori* on acidic incubation pH in the presence or absence of ureI gene (initial pH 4.0).

The microphysiometer experiments have revealed that, in nearly buffered media, acid-induced activation of urease enzyme activity of ureI knock-out mutants did not occur in media of high acidity which was in contrast to the results obtained using parental cells. In media of moderate acidity stimulation of urease activity with therefore detection of strong medium alkalinization during rate measurements was observed with both, wild-type cells as well as ureI-lacking mutants. Thus we studied how the mutants affect pH of media in the absence of strong buffers without medium perfusion in the range of moderate medium acidity as well as in media of high acidity. As controls we used parental cell populations. Results are given in FIG. 11 for media where the initial pH were adjusted to high acidity (pH 2.0) and in FIG. 12 for moderate initial medium pH (pH 4.0). The data of FIG. 11 show that H. pylori 69A elevated the pH of the incubation initially set to pH 2.0 to about pH 6.5 or 8.0 in the presence of 5 mM or 10 mM urea. In the absence of urea acidic medium pH was maintained. In contrast, the ureI-deficient mutant was not able to elevate medium pH even in the presence of 5 or 10 mM urea. Comparing H. pylori wild-type cells and the ureI-mutant there was no difference in the capability to raise pH of media containing 5 or 10 mM when this was initially set to pH 4.0, as can be seen in FIG. 12. In experiments using other ureI knock-out mutants (generated as described above) and their corresponding parental cells the same difference was found between initial medium pH 2.0 and 4.0.

In conclusion, there is a clear difference in the phenotype of mutated H. pylori cells and wild-type cells at low pH but not at moderate acidity. This difference is due to the absence of the ureI gene in the mutants. The data obtained in the above pH shift assay were in agreement with the results from our studies on the enzymatic activity of urease as well as metabolic activities of the ureI knock-out mutants and their corresponding parental cells.

In a typical pH shift assay H. pylori cells (about $10^8$/ml) are incubated in a salt solution (140 mM NaCl, 2.5 mM KCl) adjusted to pH 2 and supplemented with urea (1–20 mM) and substance (1–50 $\mu$M) to be tested. Parameters to be measured after incubation are final pH or other parameters to assay for bacterial vitality, as for example metabolic activity of cells. Such parameters can be measured as described above.

Effect of Acidic Pre-Incubation of H. pylori in Strong Buffers on Growth (Growth Assay)

In the above experiments we demonstrated the importance of ureI for stimulation and maintenance of urease activity (medium alkalinization) in media of low pH and maintenance of metabolism under the latter conditions. We also showed the ureI mutant is not able to change the pH of media adjusted to pH 2.0 but were able to elevate media pre-adjusted to pH 4.0. Here we analyzed whether the ureI-gene or gene product is an necessary factor for bacterial viability under acidic conditions. The parameter for bacterial viability assayed here was bacterial growth after acid exposure. Bacterial populations were incubated in the presence of strong buffers at pH 2.0, 3.0 and 7.0 in the absence or presence of urea (10 mM). Even in the presence of 10 mM urea there was no significant change of medium pH during incubation due to the presence of strong buffers. After 60 min of incubation aliquots were taken inoculated into fresh growth medium. Bacterial growth was detected via increase of optical density at 578 nm.

Figure 13:
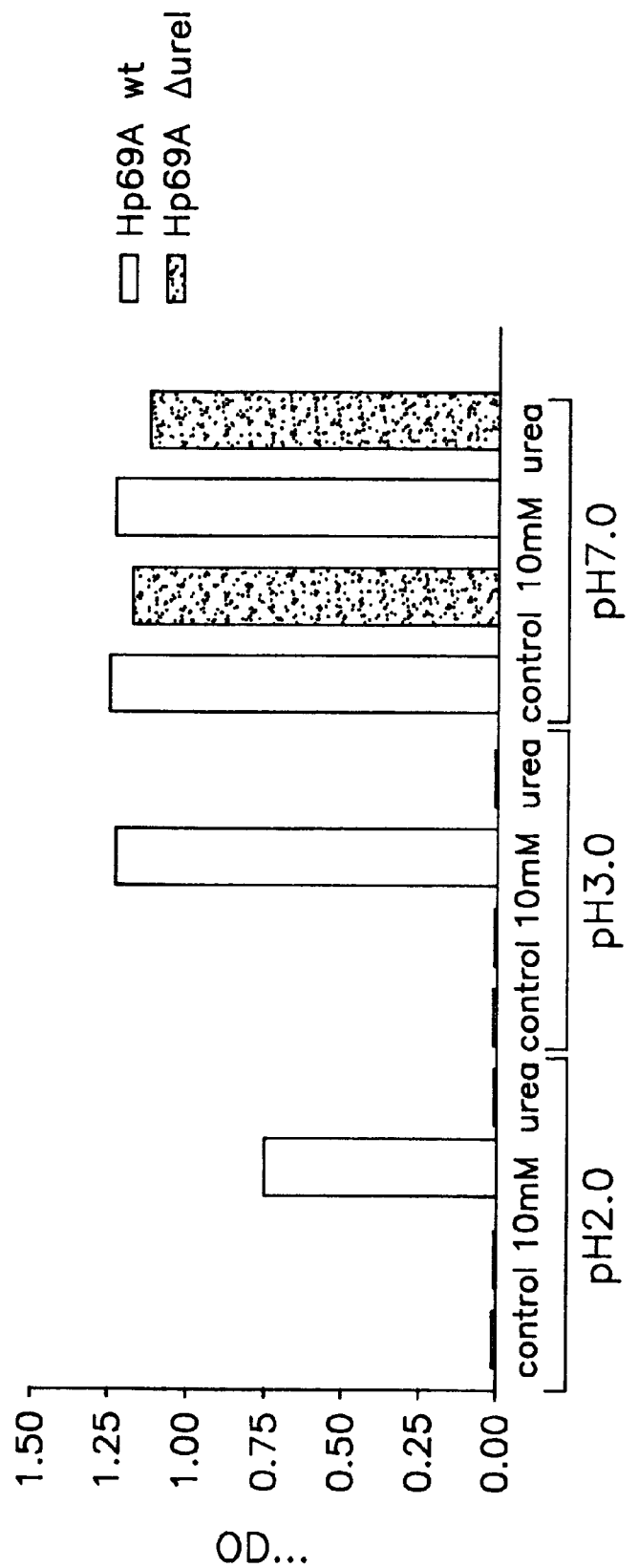
FIG. 13 illustrates growth of *H. pylori* after incubation in buffered media of acidic pH.

The data presented here are from H. pylori 69 and the corresponding ureI-lacking mutant (FIG. 13). Results obtained with the other strains used in this study are similar. As can been seen in FIG. 13 growth of H. pylori 69A wild-type cells was detected when these cells were pre-incubated at pH 2.0 as well as 3.0 in the presence of 10 mM urea but not when urea was absent during acid exposure. UreI mutants did not show growth after pH 2.0 or pH 3.0 pre-incubation in the presence of urea. The data demonstrate that the ureI knock-out are more sensitive against acid than the wild-type strain.

In a typical pH growth assay H. pylori cells are incubated in a acidic buffer (100 mM citric acid-phosphate) in the presence of urea (typically 1–20 mM) and 1–50 $\mu$M of a substance to be tested. After incubation (typically 30 min) treated cells were transferred to growth medium and cultured under standard growth conditions. Viability of cells and therefore growth can be detected by monitoring of the optical density at 578 nm or by determining vital parameters of bacterial physiology, as for example metabolic activity.

Process Based on the Detection of Urease-Mediated pH Changes in Cellular Compartments of H. pylori and/or in the Environment of H. pylori Bacteria (*H. pylori*) are placed in suspension in a microwell titer plate in basal medium containing 1–10 μM BCECF dye in acidic buffer (buffers typically to be used are given above: citric acid-phosphate, HEPES or MES in concentration range of typically 50 mM through 250 mM ) (pH<7; pH range 2 up to around 6; best between pH 3.0 through 5.0 depending on the *H. pylori* strain to be used). Urea is added at 2–10 mM, substance is added at 1 to 50 μM and after 1–5 min BCECF fluorescence is measured. The assay will also work using urea concentrations and times outside the range given above (which is worked for *H. pylori* ATCC49504). The optimal conditions for the assay is strain dependent. The increase of fluorescence at 480 nm at acidic pH (pH 4.0 works well with ATCC49504) is due to urease activity which is essentially dependent on ureI. In the absence of UreI protein function or ureI gene expression (as for example by knock-out mutagenesis) increase of fluorescence induced at acidic pH (due to presence of urea and with therefore urease activity in urease-positive *H. pylori* strains) is negatively affected or even completely inhibited (full inhibition of ureI gene product or ureI expression). Thus the presence of a potential ureI inhibitor during acidic incubation is indicated by diminished increase of BCECF fluorescence or even absence of increased fluorescence. An absence of inhibition at neutral pH (pH 7.0 where urease activity is not ureI-dependent) and inhibition at acidic pH identifies compounds that are potential inhibitors of ureI.

Process for Identification of Substances able to Activate UreI Based on the Sensitivity to Medium Urea This process makes use of the well known phenomenon that *H. pylori* is sensitive to urea in the medium in a neutral pH range. For example, the minimal inhibitory of growth of *H. pylori* 69A under standard cultivation conditions is 25 mM and the same was found for the *H. pylori* 69A ureI knock-out mutant. Thus a typical assay for substances able to activate ureI function is as follows: *H. pylori* (wild-type and ureI-mutant) is incubated in a buffer (100 mM Tris(HCl) pH 7.0) in the presence of the salts contained in BSSGG medium or weakly buffered medium (BSSGG) in the presence of non-lethal urea concentration (e.g. 15 mM for *H. pylori* 69A) and a substance to be tested for a time period required for eventual substance-induced urea toxicity which should be detectable for the wild-type strain but not for the mutant and in the absence of urea. After incubation viability of cells (eg metabolism) is measured or substance-treated *H. pylori* (wild-type and mutant) and control cells (compound treatment in the absence of urea) are transferred into growth medium and checked for growth under standard culture conditions.

DESCRIPTION OF FIGURES

FIG. 1: Organization of the urease operon in *H. pylori* wild-type cells and in ureI-deficient mutants. The figure shows the ORFs contained in the urease operon of *H. pylori* (arrows). These ORFs are ureA, ureB, ureI, ureE, ureF, ureG and ureH, as found in urease-positive *H. pylori* wild-type cells. In the ureI knock-out mutants constructed the urease operon contains the ORF of a kanamycin resistance cassette instead of the ORF of ureI (ure kanR delta ureI operon). In this mutants the kanR ORF is integral part of a modified urease operon.

FIG. 2: Expression of ureB gene product (UreB protein) in *H. pylori* cells. Cellular protein of *H. pylori* parental cell populations and of their corresponding ureI knock-out derivatives was assayed for presence of UreB via Western blot analysis. The urease protein was detected by an antiserum capable to detect urease subunit B of the *H. pylori* enzyme. Molecular weight is in kilo Dalton (kD). Cellular protein assayed was from *H. pylori* ATCC49503 (503 wt), *H. pylori* ATCC43504 (504 wt), *H. pylori* 69A (69A) and corresponding *H. pylori* gene knock-outs lacking ureI. As can be seen, the level of UreB detected in the cellular protein of the wild-type cells and ureI-deficient mutants was nearly identical.

FIG. 3: Comparison of the pH optimum of bacterial urease activity in intact organisms of *H. pylori* 69A and *H. pylori* 69A ureI knock-out mutant. Urease activities shown here were determined by urease-mediated $CO_2$ release after cleavage of radioactive labeled urea. Stimulation of urease activity at medium pH 6.0 and below was observed for *H. pylori* 69A cells but for the mutant. Moreover, there is a decrease of $CO_2$ release at pH 6.0 and 5.0, and urease activity was more or less absent at pH 4.0 and 3.0 in the mutant.

FIG. 4: Alkalinization rates of *H. pylori* 69A and corresponding mutant lacking ureI measured in a microphysiometer under acute acid exposure. Bacterial populations were initially perfused with BSSGG medium at pH 7.4 in the chambers of the microphysiometer for monitoring of medium acidification. Then these acidifying cells bacterial cells were perfused with the same medium supplemented with 2.5 mM urea and adjusted to the pH values indicated in the figure. Acute acid exposure was for 10 min and mean rates of medium alkalinization during urea pulse are shown here. Control populations of the microorganisms were exposed to the medium without urea but otherwise identical conditions. Alkalinization rates shown here are from bacterial populations of *H. pylori* 69A and *H. pylori* ureI knock-out mutant.

FIG. 5: Alkalinization rates of ureI knock-out cells of *H. pylori* ATCC49503 measured in a microphysiometer under acute acid exposure. Conditions are the same as described for *H. pylori* 69A in the legend of FIG. 4. Bacterial populations initially perfused with BSSGG medium at pH 7.4 were perfused with the same medium supplemented with 2.5 mM urea and adjusted to the pH values indicated in the figure. Acute acid exposure was for 10 min and mean rates of medium alkalinization during urea pulse are shown here. Control populations of the microorganisms were exposed to the medium without urea but otherwise identical conditions. Alkalinization rates shown here are from bacterial populations of *H. pylori* 69A. Corresponding results of the *H. pylori* ATCC49503 ureI knock-out mutant are presented in FIG. 6.

FIG. 6: Alkalinization rates of *H. pylori* ATCC49503 lacking ureI gene in a microphysiometer under acute acid exposure. Here are the results observed for the *H. pylori* ATCC strain lacking the ureI gene in the urease operon (for wild-type data see FIG. 5). The procedure and medium/pH conditions are exactly as described in the legend of FIG. 5 and are repeated here: Bacterial populations initially perfused with BSSGG medium at pH 7.4 were perfused with the same medium supplemented with 2.5 mM urea and adjusted to the pH values indicated in the figure. Acute acid exposure was for 10 min and mean rates of medium alkalinization during urea pulse are shown here. Control populations of the microorganisms were exposed to the medium without urea but otherwise identical conditions.

FIG. 7: Rates of medium alkalinization of acid-adapted *H. pylori* 69A ureI mutant in a microphysiometer during exposure to media of gradually increasing perfusion pH. *H. pylori* cells lacking ureI were exposed to gradually falling medium pH in the chambers of the microphysiometer. Initial medium pH was 7.4, the final medium pH was adjusted to pH 2.5. Perfusion was for 30 min at each pH value before switching to the next pH step for another 30 min thereby allowing gradually acid adaptation of the bacteria. Medium used was BSSGG at pH 7.4 and when cells were perfused with acidic medium (pH 5.5 and lower) this was BSSGG supplemented with 2.5 mM urea. Bacterial control populations were perfused with BSSGG medium without urea even at pH 5.5 and lower. Mean rates of medium alkalinization are shown. The results are taken from representative experiments each of which was run at least 3 times. The results obtained with the parental H. pylori 69A strain are shown in FIG. 8.

FIG. 8: Rates of medium alkalinization of pH-adapted H. pylori 69A in a microphysiometer during exposure to media of gradually increasing perfusion pH. Here we used bacteria of H. pylori 69A to challenge these to a stepwise gradient of increasing medium acidity from initial perfusion pH 7.4 through pH 2.5. Significant medium alkalinization occurred during rate measurements when 2.5 mM urea was present in the medium. Controls were perfused without urea. Further details can be taken from the legend of FIG. 7.

FIG. 9: Recovery rates of medium acidification of H. pylori 69A and the corresponding ureI knock-out strain after exposure to gradually decreasing perfusion pH. In this microphysiometer experiment H. pylori cell populations were perfused with BSSGG media adjusted to different pH. Initial medium pH was 7.4 for 30 min followed by perfusion to BSSGG pH 5.5, 5.0, 4.5, 4.0, 3.5, 3.0, and final pH 2.5. Perfusion was for 30 min at each pH value employing the pump cycle detailed under experimental procedures. Subsequently initial perfusion pH (pH 2.5) was reestablished to determine the recovery rates of acidification. These data are expressed in % of the initial metabolic rate. Perfusion at pH 5.5 and below was in the presence or absence (controls) of 2.5 mM urea. Perfusion at neutrality (pH 7.4) was in the absence of urea.

FIG. 10: Recovery rates of acidification at pH 7.4 after acute acid exposure of H. pylori 69A and ureI-lacking derivative. Experiments were performed in a cytosensor microphysiometer. H. pylori populations of the above strains were challenged to profusion pH 2.5 for 15 min., 30 min. or 60 min. Profusion medium (BSSGG) contained 2.5 mM urea. Controls were exposed to acidity in the absence of urea. Recovery rates of metabolism were determined at pH 7.4 and are given in % of the acidification rates observed before pH 2.5 exposure.

FIG. 11: pH shift assay: Effect of H. pylori on acidic incubation pH in the presence of or absence of ureI gene (initial pH 2.0). H. pylori 69A and H. pylori 69A ureI-lacking mutant were added to unbuffered pH 2.0 medium in the absence (control) or presence of 5 or 10 mM urea. Medium pH was measured 60 min after incubation. H. pylori 69A wild-type cells were able to rise the medium pH to neutrality. The ureI-mutant was not able to do this even after 90 min of incubation. pH elevation depends on ureI and urea in the medium.

FIG. 12: pH shift assay: Effect of H. pylori on acidic incubation pH in the presence of or absence of ureI gene (initial pH 4.0). H. pylori 69A and H. pylori 69A ureI-lacking mutant were added to unbuffered pH 2.0 medium in the absence (control) or presence of 5 or 10 mM urea. Medium pH was measured 60 min after incubation. Here with the medium pH set to 4.0 before addition of H. pylori cells we did not observe significant differences when comparing H. pylori 69A and the mutant. Both population led to an increase of medium pH to about 9. Thus the pH shift observed here does not depend on ureI. Controls incubated in the absence of also showed an elevation of medium pH (up to pH 5–6). But pH elevation occurred much slower than in media containing urea (data not shown).

FIG. 13: Growth of H. pylori after incubation in buffered media of acidic pH. Incubation at acidic pH was carried out in strong buffer at pH 2.0, 3.0 or 7.0 in the presence or absence of 10 mM urea. Aliquots of cells exposed to these buffers for 30 min were subsequently transferred to media required for bacterial growth. Bacteria were incubated under standard culture conditions to assay whether cells had survived acidic exposure. Growth was detected by determination of the optical density at 578 nm.

We claim:

1. A screening process for the identification of anti-helicobactericidal substances comprising treating under acidic conditions, gastric Helicobacter cells carrying a functional urease operon with at least one substance to be tested for anti-helicobactericidal activity and determining the gastric Helicobacter acid resistance.

2. The screening process according to claim 1, for the identification of substances inhibiting ureI dependent mechanisms of gastric Helicobacter metabolism.

3. The screening process according to claim 1 further comprising the step of treating, under conditions where gastric Helicobacter urease-activation is ureI-independent, gastric Helicobacter cells carrying a functional urease operon with said substance to be tested for anti-helicobactericidal activity and determining the gastric Helicobacter urease activity.

4. The screening process according to claim 3, for the identification of substances inhibiting ureI dependent mechanisms of gastric Helicobacter metabolism.

5. The screening process according to claim 2, wherein urea is present.

6. The screening process according to claim 4, wherein urea is present.

7. The screening process according to claim 2, wherein the gastric Helicobacter is *Helicobacter pylori*.

8. The screening process according to claim 4, wherein the gastric Helicobacter is *Helicobacter pylori*.

9. The screening process according to claim 2, wherein the process is carried out in a strong buffer and in the presence of urea, and gastric Helicobacter acid resistance is determined by measuring urease-mediated pH changes in cellular compartments or in the environment of gastric Helicobacter.

10. The screening process according to claim 4, wherein the process is carried out in a strong buffer and in the presence of urea, and gastric Helicobacter acid resistance is determined by measuring urease-mediated pH changes in cellular compartments or in the environment of gastric Helicobacter.

11. The screening process according to claim 2, wherein the process is carried out in an aqueous medium comprising urea and having a pH between 2 and 4, and gastric Helicobacter acid resistance is determined measuring gastric Helicobacter urease-mediated pH changes in the aqueous media.

12. The screening process according to claim 4, wherein the process is carried out in an aqueous medium comprising urea and having a pH between 2 and 4, and gastric Helicobacter acid resistance is determined measuring gastric Helicobacter urease-mediated pH changes in the aqueous media.

13. A screening process for the identification of anti-helicobactericidal substances comprising treating under conditions where gastric Helicobacter urease-activation is ureI-independent gastric Helicobacter cells carrying a functional urease operon with at least one substance to be tested for anti-helicobactericidal activity and determining the growth sensitivity of the gastric Helicobacter to urea.

14. The screening process according to claim 13, for the identification of substances activating ureI dependent mechanisms of gastric Helicobacter metabolism.

15. The screening process according to claim 14, wherein the gastric Helicobacter is *Helicobacter pylori*.

16. The screening process according to claim 15 carried out under conditions where a pH between 4 and 8.5 is present.

17. An anti-helicobactericidal substance identified in a process according to claim 1.

18. An anti-helicobactericidal substance identified in a process according to claim 13.

* * * * *